(12) United States Patent
Kalkum et al.

(10) Patent No.: US 8,067,192 B2
(45) Date of Patent: Nov. 29, 2011

(54) METHODS FOR DETECTION OF BOTULINUM NEUROTOXIN

(75) Inventors: Markus Kalkum, Azusa, CA (US); Karine Bagramyan, North Hollywood, CA (US)

(73) Assignee: City of Hope, Duarte, CA (US)

( * ) Notice: Subject to any disclaimer, the term of this patent is extended or adjusted under 35 U.S.C. 154(b) by 464 days.

(21) Appl. No.: 12/134,092

(22) Filed: Jun. 5, 2008

(65) Prior Publication Data

US 2009/0176259 A1 Jul. 9, 2009

Related U.S. Application Data

(60) Provisional application No. 60/942,199, filed on Jun. 5, 2007.

(51) Int. Cl.
*G01N 33/573* (2006.01)
(52) U.S. Cl. .................................................. 435/7.94
(58) Field of Classification Search .................. None
See application file for complete search history.

(56) References Cited

U.S. PATENT DOCUMENTS

| | | | | |
|---|---|---|---|---|
| 6,504,006 B1 * | 1/2003 | Shine et al. | ........... | 530/323 |
| 6,506,006 B2 | 1/2003 | Lui et al. | | |
| 6,696,304 B1 * | 2/2004 | Davies | ........... | 436/518 |
| 6,762,280 B2 * | 7/2004 | Schmidt et al. | ........... | 530/300 |
| 7,034,107 B2 * | 4/2006 | Schmidt et al. | ........... | 530/300 |
| 7,157,553 B2 * | 1/2007 | Schmidt et al. | ........... | 530/300 |
| 7,670,796 B2 * | 3/2010 | Shone et al. | ........... | 435/23 |
| 2004/0146963 A1 * | 7/2004 | Schmidt et al. | ........... | 435/23 |
| 2005/0287622 A1 * | 12/2005 | Schmidt et al. | ........... | 435/23 |
| 2008/0213255 A1 * | 9/2008 | Atassi | ........... | 424/130.1 |

OTHER PUBLICATIONS

Witcome, Matthew et al, FEMS Immunology and Medical Microbiology, vol. 24, pp. 319-323, 1999, Development of in vitro assays for the detection of botulinum toxins in foods.*
Aina, O.H. et al. From combinatorial chemistry to cancer-targeting peptides. *Mol Pharm* 4, 631-651 (2007).
Aina, O.H. et al. Identification of novel targeting peptides for human ovarian cancer cells using "one-bead one-compound" combinatorial libraries. *Mol Cancer Ther* 4, 806-813 (2005).
Aoki, K.R. & Guyer, B. Botulinum toxin type A and other botulinum toxin serotypes: a comparative review of biochemical and pharmacological actions. *Eur J Neurol* 8 Suppl 5, 21-29 (2001).
Arnon, S.S. et al. Botulinum toxin as a biological weapon: medical and public health management. *JAMA* 285, 1059-1070 (2001).
Arnon, S.S., Schechter, R., Maslanka, S.E., Jewell, N.P. & Hatheway, C.L. Human botulism immune globulin for the treatment of infant botulism. *N Engl J Med* 354, 462-471 (2006).

(Continued)

*Primary Examiner* — Albert Navarro
*Assistant Examiner* — Ginny Portner
(74) *Attorney, Agent, or Firm* — Perkins Coie LLP; Lauren Sliger

(57) ABSTRACT

Provided herein is a large immuno-sorbent surface area assay (ALISSA) for rapid and sensitive detection of toxin or enzyme activity. This assay is designed to capture a low number of toxin or enzyme molecules and to measure their intrinsic protease activity via conversion of a fluorogenic or luminescent substrate. The ALISSA is significantly faster and more sensitive than methods routinely utilized in the art. This assay is applicable for use for detection of a variety of toxins or enzymes having proteolytic activity, such as botulinum neurotoxin, *bacillus anthracis* lethal factor, human chitinases, and *aspergillus fumigatus* proteases. Also provided are methods for constructing and identifying novel luminescent or fluorescent substrates suitable for use with the ALISSA method.

16 Claims, 17 Drawing Sheets

OTHER PUBLICATIONS

Barr, J.R. et al. Botulinum neurotoxin detection and differentiation by mass spectrometry. *Emerg Infect Dis* 11, 1578-1583 (2005).

Boyer, A.E. et al. From the mouse to the mass spectrometer: detection and differentiation of the endoproteinase activities of botulinum neurotoxins A-G by mass spectrometry. *Anal Chem* 77, 3916-3924 (2005).

Cai, S. & Singh, B.R. Role of the disulfide cleavage induced molten globule state of type a botulinum neurotoxin in its endopeptidase activity. *Biochemistry* 40, 15327-15333 (2001).

Cai, S., Sarkar, H.K. & Singh, B.R. Enhancement of the endopeptidase activity of botulinum neurotoxin by its associated proteins and dithiothreitol. *Biochemistry* 38, 6903-6910 (1999).

Chao, H.Y., Wang, Y.C., Tang, S.S. & Liu, H.W. A highly sensitive immuno-polymerase chain reaction assay for *Clostridium botulinum* neurotoxin type A. *Toxicon* 43, 27-34 (2004).

Chen, F., Kuziemko, G.M. & Stevens, R.C. Biophysical characterization of the stability of the 150-kilodalton botulinum toxin, the nontoxic component, and the 900-kilodalton botulinum toxin complex species. *Infect Immun* 66, 2420-2425 (1998).

Ferreira, J.L., Maslanka, S., Johnson, E. & Goodnough, M. Detection of botulinal neurotoxins A, B, E, and F by amplified enzyme-linked immunosorbent assay: collaborative study. *J AOAC Int* 86, 314-331 (2003).

Garcia-Rodriguez, C. et al. Molecular evolution of antibody cross-reactivity for two subtypes of type A botulinum neurotoxin. *Nat Biotechnol* 25, 107-116 (2007).

Juskowiak, G.L. et al. Fluorogenic peptide sequences—transformation of short peptides into fluorophores under ambient photooxidative conditions. *J Am Chem Soc* 126, 550-556 (2004).

Kalb, S.R. et al. The use of Endopep-MS for the detection of botulinum toxins A, B, E, and F in serum and stool samples. *Anal Biochem* 351, 84-92 (2006).

Kalb, S.R., Goodnough, M.C., Malizio, C.J., Pirkle, J.L. & Barr, J.R. Detection of botulinum neurotoxin A in a spiked milk sample with subtype identification through toxin proteomics. *Anal Chem* 77, 6140-6146 (2005).

Kautter, D.A. & Solomon, H.M. Collaborative study of a method for the detection of *Clostridium botulinum* and its toxins in foods. *J Assoc Off Anal Chem* 60, 541-545 (1977).

Kurazono, H. et al. Minimal essential domains specifying toxicity of the light chains of tetanus toxin and botulinum neurotoxin type A. *J Biol Chem* 267, 14721-14729 (1992).

Lacy, D.B., Tepp, W., Cohen, A.C., DasGupta, B.R. & Stevens, R.C. Crystal structure of botulinum neurotoxin type A and implications for toxicity. *Nat Struct Biol* 5, 898-902 (1998).

Lam, K.S. et al. Synthesis and screening of "one-bead one-compound" combinatorial peptide libraries. *Methods Enzymol* 369, 298-322 (2003).

Liu, W., et al. Botulinum toxin type B micromechanosensor. *Proc Natl Acad Sci USA* 100, 13621-13625 (2003).

Marks, J.D. Deciphering antibody properties that lead to potent botulinum neurotoxin neutralization. *Mov Disord* 19 Suppl 8, S101-108 (2004).

Mason, J.T., Xu, L., Sheng, Z.M. & O'Leary, T.J. A liposome-PCR assay for the ultrasensitive detection of biological toxins. *Nat Biotechnol* 24, 555-557 (2006).

Mason, J.T., Xu, L., Sheng, Z.M., He, J. & O'Leary, T.J. Liposome polymerase chain reaction assay for the sub-attomolar detection of cholera toxin and botulinum neurotoxin type A. *Nature Protocols* 1, 2003-2011 (2006).

Melling, J., Hambleton, P. & Shone, C.C. *Clostridium botulinum* toxins: nature and preparation for clinical use. *Eye* 2 ( Pt 1), 16-23 (1988).

Miyawaki, A. Bringing bioluminescence into the picture. *Nat Methods* 4, 616-617 (2007).

Paulmurugan, R. et al. Combinatorial library screening for developing an improved split-firefly luciferase fragment-assisted complementation system for studying protein-protein interactions. *Anal Chem* 79, 2346-2353 (2007).

Paulmurugan, R. et al. Firefly luciferase enzyme fragment complementation for imaging in cells and living animals. *Anal Chem* 77, 1295-1302 (2005).

Ravichandran, E. et al. An initial assessment of the systemic pharmacokinetics of botulinum toxin. *J Pharmacol Exp Ther* 318,1343-1351 (2006).

Rosse, G.E. et al. Rapid identification of substrates for novel proteases using a combinatorial peptide library. *J Comb Chem* 2, 461-466 (2000).

Sakaguchi, G. *Clostridium botulinum* toxins. *Pharmacol Ther* 19, 165-194 (1982).

Schantz, E.J. & Johnson, E.A. Properties and use of botulinum toxin and other microbial neurotoxins in medicine. *Microbiol Rev* 56, 80-99 (1992).

Schiavo, G. et al. Botulinum neurotoxins serotypes A and E cleave SNAP-25 at distinct COOH-terminal peptide bonds. *FEBS Lett* 335, 99-103 (1993).

Schiavo, G. et al. Identification of the nerve terminal targets of botulinum neurotoxin serotypes A, D, and E. *J Biol Chem* 268, 23784-23787 (1993).

Schiavo, G., Matteoli, M. & Montecucco, C. Neurotoxins affecting neuroexocytosis. *Physiol Rev* 80, 717-766 (2000).

Schmidt, J.J. & Stafford, R.G. Fluorigenic substrates for the protease activities of botulinum neurotoxins, serotypes A, B, and F. *Appl Environ Microbiol* 69, 297-303 (2003).

Sharma, S.K., Ferreira, J.L., Eblen, B.S. & Whiting, R.C. Detection of type A, B, E, and F *Clostridium botulinum* neurotoxins in foods by using an amplified enzyme-linked immunosorbent assay with digoxigenin-labeled antibodies. *Appl Environ Microbiol* 72, 1231-1238 (2006).

Sharma, S.K., Ramzan, M.A. & Singh, B.R. Separation of the components of type A botulinum neurotoxin complex by electrophoresis. *Toxicon* 41, 321-331 (2003).

Simpson, L.L. et al. The role of zinc binding in the biological activity of botulinum toxin. *J Biol Chem* 276, 27034-27041 (2001).

Smith, L.D. The occurrence of *Clostridium botulinum* and *Clostridium tetani* in the soil of the United States. *Health Lab Sci* 15, 74-80 (1978).

Walsh, T.J. et al. Tissue homogenization with sterile reinforced polyethylene bags for quantitative culture of *Candida albicans*. *J Clin Microbiol* 25, 931-932 (1987).

Wein, L.M. & Liu, Y. Analyzing a bioterror attack on the food supply: the case of botulinum toxin in milk. *Proc Natl Acad Sci U S A* 102, 9984-9989 (2005).

Zhang, L., Lin, W.J., Li, S. & Aoki, K.R. Complete DNA sequences of the botulinum neurotoxin complex of *Clostridium botulinum* type A-Hall (Allergan) strain. *Gene* 315, 21-32 (2003).

* cited by examiner

A  protein A    anti-BoNT/A
   beads        antibodies

1.) binding

2.) cross linking

3.) washing

BoNT/A
immuno-affinity matrix

B

BoNT/A quenched
fluorigenic
reporter cleaved
fluorescent
reporter

BoNT/A in 10% FBS as:
- ▼ pre-act. complex[a]
- ▲ non-pre-act. complex[a]
- ▶ pre-act. holotoxin[b]
- ● pre-act. holotoxin[a]
- ◀ non-preact. holotoxin[b]
- ■ non-pre-act. holotoxin[a]

B

BoNT/A complex in:
- ■ human serum
- ▶ carrot juice
- ▲ GPD
- ◀ reconstituted milk
- ▼ fresh milk

Figure 4 captured botulinum toxin reporter molecules bead surface chemical anchor antibody toxin-reacted reporter molecules give fluorescent signal

FIGURE 7

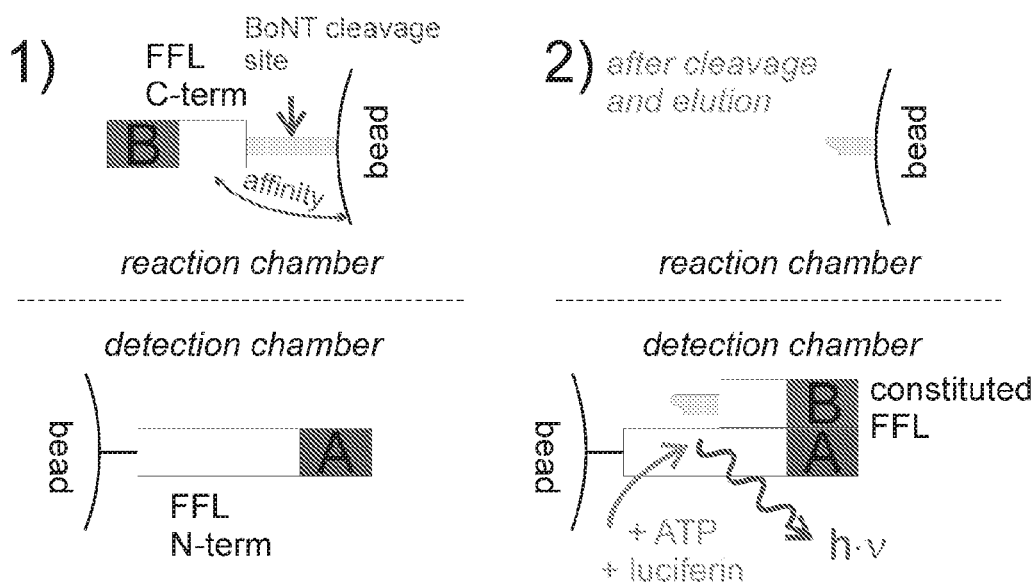
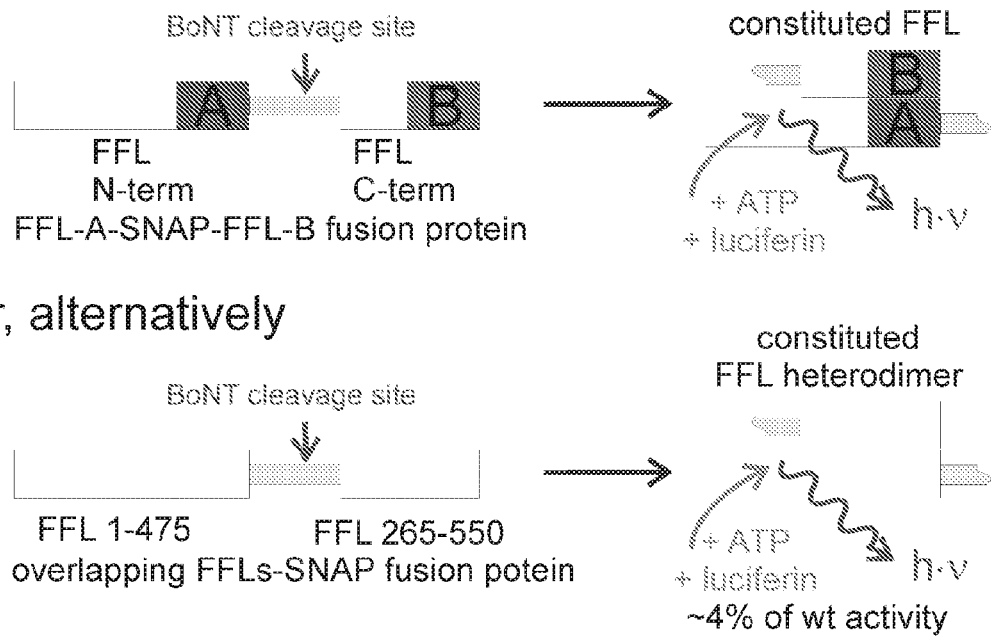
FIGURE 11

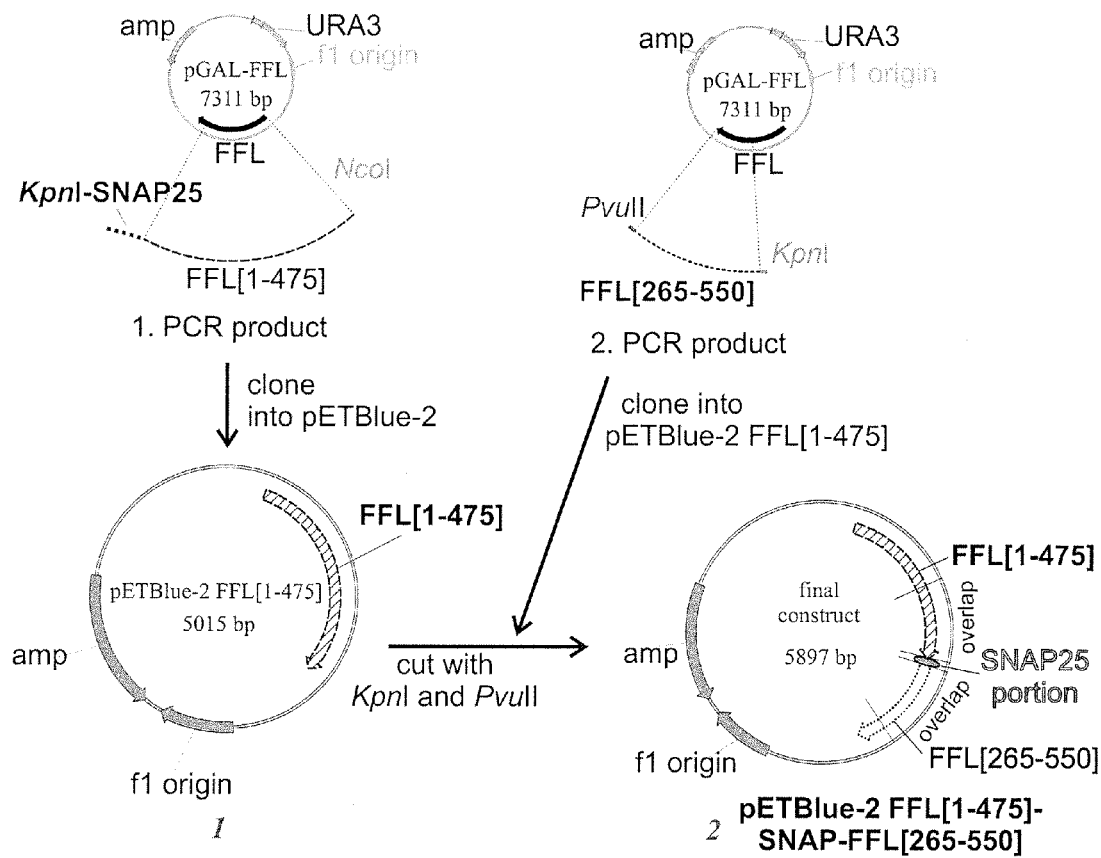
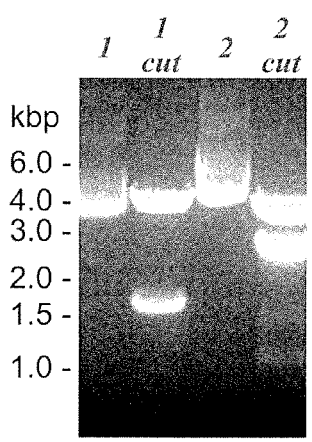
Figure 12

FFL[1-478] SNAP25(part) FFL[265-550]-histag atggaagacgccaaaaacataaagaaaggcccggcgccattctatcctctagaggatggaaccgctggagagcaactgcata
aggctatgaagagatacgccctggttcctggaacaattgcttttacagatgcacatatcgaggtgaacatcacgtacgcggaata
cttcgaaatgtccgttcggttggcagaagctatgaaacgatatgggctgaatacaaatcacagaatcgtcgtatgcagtgaaaact
ctcttcaattctttatgccggtgttgggcgcgttatttatcggagttgcagttgcgcccgcgaacgacatttataatgaacgtgaattg
ctcaacagtatgaacatttcgcagcctaccgtagtgtttgtttccaaaaaggggttgcaaaaaattttgaacgtgcaaaaaaaattac
caataatccagaaaattattatcatggattctaaaacggattaccagggatttcagtcgatgtacacgttcgtcacatctcatctacct
cccggttttaatgaatacgattttgtaccagagtcctttgatcgtgacaaaacaattgcactgataatgaattcctctggatctactgg
gttacctaagggtgtggcccttccgcatagaactgcctgcgtcagattctcgcatgccagagatcctattttggcaatcaaatcatt
ccggatactgcgattttaagtgttgttccattccatcacggttttggaatgtttactacactcggatatttgatatgtggatttcgagtcg
tcttaatgtatagatttgaagaagagctgtttttacgatcccttcaggattacaaaattcaaagtgcgttgctagtaccaaccctatttc
attcttcgccaaaagcactctgattgacaaatacgatttatctaatttacacgaaattgcttctgggggcgcacctctttcgaaagaa
gtcggggaagcggttgcaaaacgcttccatcttccagggatacgacaaggatatgggctcactgagactacatcagctattctga
ttacacccgaggggatgataaaccgggcgcggtcggtaaagttgttccattttttgaagcgaaggttgtggatctggataccgg
gaaaacgctgggcgttaatcagagaggcgaattatgtgtcagaggacctatgattatgtccggttatgtaaacaatccggaagcg
accaacgccttgattgacaaggatggatggctacattctggagacatagcttactgggacgaagacgaacacttcttcatagttga
ccgcttgaagtctttaattaaatacaaaggatatcaggtggccccccgctgaattggaatcgatattgttacaacaccccaacatcttc
gacgcgggcgtggcaggtcttcccgacgatgacgccggg**AGCAACAAAACCCGTATTGATGAAG
CGAACCAGCGTGCGACCAAAATGCTG**atgtatagatttgaagaagagctgtttttacgatcccttcag
gattacaaaattcaaagtgcgttgctagtaccaaccctatttcattcttcgccaaaagcactctgattgacaaatacgatttatctaat
ttacacgaaattgcttctgggggcgcacctctttcgaaagaagtcggggaagcggttgcaaaacgcttccatcttccagggatac
gacaaggatatgggctcactgagactacatcagctattctgattacacccgaggggatgataaaccgggcgcggtcggtaaa
gttgttccattttttgaagcgaaggttgtggatctggataccgggaaaacgctgggcgttaatcagagaggcgaattatgtgtcag
aggacctatgattatgtccggttatgtaaacaatccggaagcgaccaacgccttgattgacaaggatggatggctacattctggag
acatagcttactgggacgaagacgaacacttcttcatagttgaccgcttgaagtctttaattaaatacaaaggatatcaggtggccc
ccgctgaattggaatcgatattgttacaacaccccaacatcttcgacgcgggcgtggcaggtcttcccgacgatgacgccggtg
aacttcccgccgccgttgttgtttggagcacggaaagacgatgacggaaaaagagatcgtggattacgtcgccagtcaagtaa
caaccgcgaaaaagttgcgcggaggagttgtgtttgtggacgaagtaccgaaaggtcttaccggaaaactcgacgcaagaaaa
atcagagagatcctcataaaggccaagaagggcggaaagtccgagttg*ctcgagcaccaccaccaccaccactga*

FIGURE 13

FFL[1-478] SNAP25(part) FFL[265-550]-histag

MEDAKNIKKGPAPFYPLEDGTAGEQLHKAMKRYALVPGTIAFTDAHIEVNITYA
EYFEMSVRLAEAMKRYGLNTNHRIVVCSENSLQFFMPVLGALFIGVAVAPANDI
YNERELLNSMNISQPTVVFVSKKGLQKILNVQKKLPIIQKIIIMDSKTDYQGFQSM
YTFVTSHLPPGFNEYDFVPESFDRDKTIALIMNSSGSTGLPKGVALPHRTACVRFS
HARDPIFGNQIIPDTAILSVVPFHHGFGMTTLGYLICGFRVVLMYRFEEELFLRSL
QDYKIQSALLVPTLFSFFAKSTLIDKYDLSNLHEIASGGAPLSKEVGEAVAKRFHL
PGIRQGYGLTETTSAILITPEGDDKPGAVGKVVPFFEAKVVDLDTGKTLGVNQRG
ELCVRGPMIMSGYVNNPEATNALIDKDGWLHSGDIAYWDEDEHFFIVDRLKSLI
KYKGYQVAPAELESILLQHPNIFDAGVAGLPDDDAGSNKTRIDEANQRATKML
MYRFEEELFLRSLQDYKIQSALLVPTLFSFFAKSTLIDKYDLSNLHEIASGGAPLSK
EVGEAVAKRFHLPGIRQGYGLTETTSAILITPEGDDKPGAVGKVVPFFEAKVVDL
DTGKTLGVNQRGELCVRGPMIMSGYVNNPEATNALIDKDGWLHSGDIAYWDED
EHFFIVDRLKSLIKYKGYQVAPAELESILLQHPNIFDAGVAGLPDDDAGELPAAV
VVLEHGKTMTEKEIVDYVASQVTTAKKLRGGVVFVDEVPKGLTGKLDARKIREI
LIKAKKGGKSEL*LEHHHHHH**

FIGURE 14

MAEDADMRNELEEMQRRADQLADESLESTRRMLQLVEESKDAGIRTLVMLDEQGEQLERIEEG
MDQINKDMKEAEKNLTDLGKFCGLCVCPCNKLKSSDAYKKAWGNNQDGVVASQPARVVDERE
QMAISGGFIRRVTNDARENEMDENLEQVSGIIGNLRHMALDMGNEIDTQNRQIDRIMEKADSNKT
RIDEANQRATKMLGSG

FIGURE 15

```
                              SEQUENCE LISTING

<160> NUMBER OF SEQ ID NOS: 22

<210> SEQ ID NO 1
<211> LENGTH: 17
<212> TYPE: PRT
<213> ORGANISM: Artificial Sequence
<220> FEATURE:
<223> OTHER INFORMATION: SNAP25 insert

<400> SEQUENCE: 1

Ser Asn Lys Thr Arg Ile Asp Glu Ala Asn Gln Arg Ala Thr Lys Met
1               5                   10                  15

Leu

<210> SEQ ID NO 2
<211> LENGTH: 10
<212> TYPE: PRT
<213> ORGANISM: Artificial Sequence
<220> FEATURE:
<223> OTHER INFORMATION: Botulinum Neurotoxin serotype A (BoNT/A)
      cleavage and recognition site

<400> SEQUENCE: 2

Ile Asp Glu Ala Asn Gln Arg Ala Thr Lys
1               5                   10

<210> SEQ ID NO 3
<211> LENGTH: 2370
<212> TYPE: DNA
<213> ORGANISM: Artificial Sequence
<220> FEATURE:
<223> OTHER INFORMATION: FFL fusion protein

<400> SEQUENCE: 3
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggcccct ccgcatagaa ctgcctgcgt cagattctcg     660
catgccagag atcctatttt tggcaatcaa atcattccgg atactgcgat tttaagtgtt     720
gttccattcc atcacggttt tggaatgttt actacactcg gatatttgat atgtggattt     780
cgagtcgtct taatgtatag atttgaagaa gagctgtttt tacgatccct tcaggattac     840
```

-continued

```
aaaattcaaa gtgcgttgct agtaccaacc ctatttcat tcttcgccaa aagcactctg      900
attgacaaat acgatttatc taatttacac gaaattgctt ctgggggcgc acctctttcg      960
aaagaagtcg gggaagcggt tgcaaaacgc ttccatcttc cagggatacg acaaggatat     1020
gggctcactg agactacatc agctattctg attacacccg aggggatga taaaccgggc      1080 gcggtcggta agttgttcc attttttgaa gcgaaggttg tggatctgga taccgggaaa      1140
acgctgggcg ttaatcagag aggcgaatta tgtgtcagag acctatgat tatgtccggt      1200 tatgtaaaca atccggaagc gaccaacgcc ttgattgaca aggatggatg ctacattct      1260 ggagacatag cttactggga cgaagacgaa cacttcttca tagttgaccg cttgaagtct     1320
ttaattaaat acaaaggata tcaggtggcc cccgctgaat tggaatcgat attgttacaa     1380 cacccccaaca tcttcgacgc gggcgtggca ggtcttcccg acgatgacgc cgggagcaac     1440
aaaacccgta ttgatgaagc gaaccagcgt gcgaccaaaa tgctgatgta tagatttgaa     1500
gaagagctgt ttttacgatc ccttcaggat tacaaaattc aaagtgcgtt gctagtacca     1560
accctatttt cattcttcgc caaaagcact ctgattgaca aatacgattt atctaattta     1620
cacgaaattg cttctgggggg cgcacctctt tcgaaagaag tcggggaagc ggttgcaaaa     1680
cgcttccatc ttccagggat acgacaagga tatgggctca ctgagactac atcagctatt     1740
ctgattacac ccgaggggga tgataaaccg ggcgcggtcg gtaaagttgt tccatttttt     1800
gaagcgaagg ttgtggatct ggataccggg aaaacgctgg gcgttaatca gagaggcgaa     1860
ttatgtgtca gaggacctat gattatgtcc ggttatgtaa caatccgga agcgaccaac     1920 gccttgattg acaaggatgg atggctacat tctggagaca tagcttactg ggacgaagac     1980
gaacacttct tcatagttga ccgcttgaag tctttaatta aatacaaagg atatcaggtg     2040 gccccgctg aattggaatc gatattgtta caacacccca acatcttcga cgcgggcgtg     2100
gcaggtcttc ccgacgatga cgccggtgaa cttcccgccg ccgttgttgt tttggagcac     2160
ggaaagacga tgacggaaaa agagatcgtg gattacgtcg ccagtcaagt aacaaccgcg     2220
aaaaagttgc gcggaggagt gtgtttgtg gacgaagtac cgaaaggtct taccggaaaa     2280
ctcgacgcaa gaaaaatcag agagatcctc ataaaggcca gaagggcgg aaagtccgag     2340 ttgctcgagc accaccacca ccaccactga                                      2370
```

<210> SEQ ID NO 4
<211> LENGTH: 789
<212> TYPE: PRT
<213> ORGANISM: Artificial Sequence
<220> FEATURE:
<223> OTHER INFORMATION: FFL1-478SNAP25FFL265-550

<400> SEQUENCE: 4

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

-continued

```
Phe Ile Gly Val Ala Val Ala Pro Ala Asn Asp Ile Tyr Asn Glu Arg
                100                 105                 110
Glu Leu Leu Asn Ser Met Asn Ile Ser Gln Pro Thr Val Phe Val
            115                 120                 125
Ser Lys Lys Gly Leu Gln Lys Ile Leu Asn Val Gln Lys Lys Leu Pro
        130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Thr Ala Cys Val Arg Phe Ser His Ala Arg Asp
210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
            290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
        435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Ala Gly Ser Asn
465                 470                 475                 480
Lys Thr Arg Ile Asp Glu Ala Asn Gln Arg Ala Thr Lys Met Leu Met
                485                 490                 495
Tyr Arg Phe Glu Glu Glu Leu Phe Leu Arg Ser Leu Gln Asp Tyr Lys
            500                 505                 510
Ile Gln Ser Ala Leu Leu Val Pro Thr Leu Phe Ser Phe Phe Ala Lys
        515                 520                 525
```

```
Ser Thr Leu Ile Asp Lys Tyr Asp Leu Ser Asn Leu His Glu Ile Ala
    530                 535                 540

Ser Gly Gly Ala Pro Leu Ser Lys Glu Val Gly Glu Ala Val Ala Lys
545                 550                 555                 560

Arg Phe His Leu Pro Gly Ile Arg Gln Gly Tyr Gly Leu Thr Glu Thr
                565                 570                 575

Thr Ser Ala Ile Leu Ile Thr Pro Glu Gly Asp Asp Lys Pro Gly Ala
            580                 585                 590

Val Gly Lys Val Val Pro Phe Phe Glu Ala Lys Val Val Asp Leu Asp
        595                 600                 605

Thr Gly Lys Thr Leu Gly Val Asn Gln Arg Gly Glu Leu Cys Val Arg
    610                 615                 620

Gly Pro Met Ile Met Ser Gly Tyr Val Asn Asn Pro Glu Ala Thr Asn
625                 630                 635                 640

Ala Leu Ile Asp Lys Asp Gly Trp Leu His Ser Gly Asp Ile Ala Tyr
                645                 650                 655

Trp Asp Glu Asp Glu His Phe Phe Ile Val Asp Arg Leu Lys Ser Leu
            660                 665                 670

Ile Lys Tyr Lys Gly Tyr Gln Val Ala Pro Ala Glu Leu Glu Ser Ile
        675                 680                 685

Leu Leu Gln His Pro Asn Ile Phe Asp Ala Gly Val Ala Gly Leu Pro
    690                 695                 700

Asp Asp Asp Ala Gly Glu Leu Pro Ala Ala Val Val Val Leu Glu His
705                 710                 715                 720

Gly Lys Thr Met Thr Glu Lys Glu Ile Val Asp Tyr Val Ala Ser Gln
                725                 730                 735

Val Thr Thr Ala Lys Lys Leu Arg Gly Gly Val Val Phe Val Asp Glu
            740                 745                 750

Val Pro Lys Gly Leu Thr Gly Lys Leu Asp Ala Arg Lys Ile Arg Glu
        755                 760                 765

Ile Leu Ile Lys Ala Lys Lys Gly Gly Lys Ser Glu Leu Leu Glu His
    770                 775                 780

His His His His His
785

<210> SEQ ID NO 5
<211> LENGTH: 13
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc_feature
<222> LOCATION: (1)..(1)
<223> OTHER INFORMATION: Thr at position 1 is a Thr with 4-
      Methylumbelliferone conjugated to its N-terminal ("4-MU")
<220> FEATURE:
<221> NAME/KEY: misc_feature
<222> LOCATION: (12)..(12)
<223> OTHER INFORMATION: Lys at position 12 is a Lys with 4-
      (dimethylaminoazo) benzene-4-carboxyl (DABCYL) conjugated to its
      epsilon-amino group ("Lys[DABCYL]")
<220> FEATURE:
<221> NAME/KEY: misc_feature
<222> LOCATION: (13)..(13)
<223> OTHER INFORMATION: Xaa at position 13 is 6-aminohexanoic acid

<400> SEQUENCE: 5

Thr Arg Ile Asp Glu Ala Asn Gln Arg Ala Thr Lys Xaa
1               5                   10
```

<210> SEQ ID NO 6
<211> LENGTH: 51
<212> TYPE: DNA
<213> ORGANISM: Artificial Sequence
<220> FEATURE:
<223> OTHER INFORMATION: Botulinum Neurotoxin serotype A (BoNT/A)
      cleavage site

<400> SEQUENCE: 6
agcaacaaaa cccgtattga tgaagcgaac cagcgtgcga ccaaaatgct g        51

<210> SEQ ID NO 7
<211> LENGTH: 80
<212> TYPE: DNA
<213> ORGANISM: Artificial Sequence
<220> FEATURE:
<223> OTHER INFORMATION: primer

<400> SEQUENCE: 7
atcgatggta cccagcattt tggtcgcacg ctggttcgct tcatcaatac gggttttgtt    60
gctatcgtcg ggaagacctg                                               80

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
tcttaatgta tagatttgaa gaagagctgt tttta                              35

<210> SEQ ID NO 9
<211> LENGTH: 5015
<212> TYPE: DNA
<213> ORGANISM: Artificial Sequence
<220> FEATURE:
<223> OTHER INFORMATION: plasmid "1"

<400> SEQUENCE: 9
taatacgact cactataggg gaattgtgag cggataacaa ttcccctcta gacttacaat    60
ttccattcgc cattcaggct gcgcaactgt tgggaagggc gatcggtacg ggcctcttcg   120
ctattacgcc agcttgcgaa cggtgggtgc gctgcaaggc gattaagttg ggtaacgcca   180
ggattctccc agtcacgacg ttgtaaaacg acggccagcg agatcttg attggctagc    240 agaataattt tgtttaactt taagaaggag atataccatg gaagacgcca aaaacataaa    300
gaaaggcccg gcgccattct atcctctaga ggatggaacc gctggagagc aactgcataa    360
ggctatgaag agatacgccc tggttcctgg aacaattgct tttacagatg cacatatcga    420
ggtgaacatc acgtacgcgg aatacttcga aatgtccgtt cggttggcag aagctatgaa    480
acgatatggg ctgaatacaa atcacagaat cgtcgtatgc agtgaaaact ctcttcaatt    540
ctttatgccg gtgttgggcg cgttatttat cggagttgca gttgcgcccg cgaacgacat    600
ttataatgaa cgtgaattgc tcaacagtat gaacatttcg cagcctaccg tagtgtttgt    660
ttccaaaaag gggttgcaaa aattttgaa cgtgcaaaaa aattaccaa taatccagaa    720 aattattatc atggattcta aaacggatta ccagggattt cagtcgatgt acacgttcgt    780
cacatctcat ctacctcccg gttttaatga atacgatttt gtaccagagt cctttgatcg    840
tgacaaaaca attgcactga taatgaattc ctctggatct actgggttac ctaagggtgt    900

```
ggcccttccg catagaactg cctgcgtcag attctcgcat gccagagatc ctattttt gg    960
caatcaaatc attccggata ctgcgatttt aagtgttgtt ccattccatc acggttttgg    1020
aatgtttact acactcggat atttgatatg tggatttcga gtcgtcttaa tgtatagatt    1080
tgaagaagag ctgttttttac gatcccttca ggattacaaa attcaaagtg cgttgctagt    1140
accaaccta ttttcattct tcgccaaaag cactctgatt gacaaatacg atttatctaa    1200
tttacacgaa attgcttctg ggggcgcacc tctttcgaaa aagtcggggg aagcggttgc    1260
aaaacgcttc catcttccag ggatacgaca aggatatggg ctcactgaga ctacatcagc    1320
tattctgatt acacccgagg gggatgataa accgggcgcg gtcggtaaag ttgttccatt    1380
ttttgaagcg aaggttgtgg atctggatac cgggaaaacg ctgggcgtta atcagagagg    1440
cgaattatgt gtcagaggac ctatgattat gtccggttat gtaaacaatc cggaagcgac    1500
caacgccttg attgacaagg atggatggct acattctgga gacatagctt actgggacga    1560
agacgaacac ttcttcatag ttgaccgctt gaagtcttta attaaataca aaggatatca    1620
ggtggccccc gctgaattgg aatcgatatt gttacaacac cccaacatct tcgacgcggg    1680
cgtggcaggt cttcccgacg atggtaccat cgatacgcgt tcgaagcttg cggccgcaca    1740
gctgtataca cgtgcaagcc agccagaact cgctcctgaa gacccagagg atctcgagca    1800
ccaccaccac caccactaat gttaattaag ttgggcgttg taatcatagt cataatcaat    1860
actcctgact gcgttagcaa tttaactgtg ataaactacc gcattaaagc tattcgatga    1920
taagctgtca acatgataa ttcttgaaga cgaaagggcc taggctgata aaacagaatt    1980
tgcctggcgg cagtagcgcg gtggtcccac ctgaccccat gccgaactca gaagtgaaac    2040
gccgtagcgc cgatggtagt gtggggtctc cccatgcgag agtagggaac tgccaggcat    2100
caaataaaac gaaaggctca gtcgaaagac tgggcctttc gttttatctg ttgtttgtcg    2160
gtgaacgctc tcctgagtag gacaaatccg ccgggagcgg atttgaacgt tgcgaagcaa    2220
cggcccggag ggtggcgggc aggacgcccg ccataaactg ccaggcatca aattaagcag    2280
aaggccatcc tgacggatgg ccttttt gcg tttctacaaa ctcttttgtt tattttt cta    2340
aatacattca aatatgtatc cgctgagcaa taactagcat aacccccttgg ggcctctaaa    2400
cgggtcttga ggggttttt gctgaaagga ggaactatat ccggattggc gaatgggacg    2460
cgccctgtag cggcgcatta agcgcggcgg gtgtggtggt tacgcgcagc gtgaccgcta    2520
cacttgccag cgccctagcg cccgctcctt tcgctttctt cccttccttt ctcgccacgt    2580
tcgccggctt tccccgtcaa gctctaaatc ggggg ctccc tttagggttc cgatttagtg    2640
ctttacggca cctcgacccc aaaaaacttg attagggtga tggttcacgt agtgggccat    2700
cgccctgata gacggttttt cgccctttga cgttggagtc cacgttcttt aatagtggac    2760
tcttgttcca aactggaaca cactcaacc ctatctcggt ctattctttt gatttataag    2820
ggattttgcc gatttcggcc tattggttaa aaaatgagct gatttaacaa aaatttaacg    2880
cgaattttaa caaaatatta acgtttacaa tttctggcgg cacgatggca tgagattatc    2940
aaaaaggat c ttcacctaga tccttttaaa ttaaaaatga agttttaaat caatctaaag    3000
tatatatgag taaacttggt ctgacagtta ccaatgctta atcagtgagg cacctatctc    3060
agcgatctgt ctatttcgtt catccatagt tgcctgactc ccgtcgtgt agataactac    3120
gatacgggag ggcttaccat ctggccccag tgctgcaatg ataccgcgag acccacgctc    3180
accggctcca gatttatcag caataaacca gccagccgga agggccgagc gcagaagtgg    3240
tcctgcaact ttatccgcct ccatccagtc tattaattgt tgccgggaag ctagagtaag    3300
```

```
tagttcgcca gttaatagtt tgcgcaacgt tgttgccatt gctacaggca tcgtggtgtc    3360
acgctcgtcg tttggtatgg cttcattcag ctccggttcc caacgatcaa ggcgagttac    3420
atgatccccc atgttgtgca aaaaagcggt tagctccttc ggtcctccga tcgttgtcag    3480
aagtaagttg gccgcagtgt tatcactcat ggttatggca gcactgcata attctcttac    3540
tgtcatgcca tccgtaagat gcttttctgt gactggtgag tactcaacca agtcattctg    3600
agaatagtgt atgcggcgac cgagttgctc ttgcccggcg tcaatacggg ataataccgc    3660
gccacatagc agaactttaa aagtgctcat cattggaaaa cgttcttcgg ggcgaaaact    3720
ctcaaggatc ttaccgctgt tgagatccag ttcgatgtaa cccactcgtg cacccaactg    3780
atcttcagca tcttttactt tcaccagcgt ttctgggtga gcaaaacag gaaggcaaaa    3840 tgccgcaaaa aagggaataa gggcgacacg gaaatgttga atactcatac tcttccttt     3900 tcaatcatga ccaaaatccc ttaacgtgag ttttcgttcc actgagcgtc agaccccgta    3960
gaaaagatca aaggatcttc ttgagatcct ttttttctgc gcgtaatctg ctgcttgcaa    4020
acaaaaaaac caccgctacc agcggtggtt tgtttgccgg atcaagagct accaactctt    4080
tttccgaagg taactggctt cagcagagcg cagataccaa atactgtcct tctagtgtag    4140
ccgtagttag gccaccactt caagaactct gtagcaccgc ctacatacct cgctctgcta    4200
atcctgttac cagtggctgc tgccagtggc gataagtcgt gtcttaccgg gttggactca    4260
agacgatagt taccggataa ggcgcagcgg tcgggctgaa cggggggttc gtgcacacag    4320
cccagcttgg agcgaacgac ctacaccgaa ctgagatacc tacagcgtga gctatgagaa    4380
agcgccacgc ttcccgaagg gagaaaggcg gacaggtatc cggtaagcgg cagggtcgga    4440
acaggagagc gcacgaggga gcttccaggg ggaaacgcct ggtatcttta tagtcctgtc    4500
gggtttcgcc acctctgact tgagcgtcga ttttgtgat gctcgtcagg ggggcggagc     4560
ctatggaaaa acgccagcaa cgcggccttt ttacggttcc tggccttttg ctggccttt     4620 gctcacatgt tctttcctgc gttatcccct gattctgtgg ataaccgtat taccgccttt    4680
gagtgagctg ataccgctcg ccgcagccga acgaccgagc gcagcgagtc agtgagcgag    4740
gaagccggcg ataatggcct gcttctcgcc gaaacgtttg gtggcgggac cagtgacgaa    4800
ggcttgagcg agggcgtgca agattccgaa taccgcaagc gacaggccga tcatcgtcgc    4860
gctccagcga aagcggtcct cgccgaaaat gacccagagc gctgccggca cctgtcctac    4920
gagttgcatg ataaagaaga cagtcataag tgcggcgacg accggtgaat tgtgagcgct    4980
cacaattctc gtgacatcat aacgtcccgc gaaat                               5015
```

<210> SEQ ID NO 10
<211> LENGTH: 5897
<212> TYPE: DNA
<213> ORGANISM: Artificial Sequence
<220> FEATURE:
<223> OTHER INFORMATION: plasmid "2"

<400> SEQUENCE: 10

```
taatacgact cactataggg gaattgtgag cggataacaa ttcccctcta gacttacaat      60
ttccattcgc cattcaggct gcgcaactgt tgggaagggc gatcggtacg ggcctcttcg     120
ctattacgcc agcttgcgaa cggtgggtgc gctgcaaggc gattaagttg ggtaacgcca     180
ggattctccc agtcacgacg ttgtaaaacg acggccagcg agagatcttg attggctagc     240
agaataattt tgtttaactt taagaaggag atataccatg gaagacgcca aaaacataaa     300
gaaaggcccg gcgccattct atcctctaga ggatggaacc gctggagagc aactgcataa     360
```

```
ggctatgaag agatacgccc tggttcctgg aacaattgct tttacagatg cacatatcga    420
ggtgaacatc acgtacgcgg aatacttcga aatgtccgtt cggttggcag aagctatgaa    480
acgatatggg ctgaatacaa atcacagaat cgtcgtatgc agtgaaaact ctcttcaatt    540
ctttatgccg gtgttgggcg cgttatttat cggagttgca gttgcgcccg cgaacgacat    600
ttataatgaa cgtgaattgc tcaacagtat gaacatttcg cagcctaccg tagtgtttgt    660
ttccaaaaag gggttgcaaa aaattttgaa cgtgcaaaaa aaattaccaa taatccagaa    720
aattattatc atggattcta aaacggatta ccagggattt cagtcgatgt acacgttcgt    780
cacatctcat ctacctcccg gttttaatga atacgatttt gtaccagagt cctttgatcg    840
tgacaaaaca attgcactga taatgaattc ctctggatct actgggttac ctaagggtgt    900
ggcccttccg catagaactg cctgcgtcag attctcgcat gccagagatc ctattttgg     960 caatcaaatc attccggata ctgcgatttt aagtgttgtt ccattccatc acggttttgg   1020
aatgtttact acactcggat atttgatatg tggatttcga gtcgtcttaa tgtatagatt   1080
tgaagaagag ctgttttac gatcccttca ggattacaaa attcaaagtg cgttgctagt    1140
accaacccta ttttcattct tcgccaaaag cactctgatt gacaaatacg atttatctaa   1200
tttacacgaa attgcttctg ggggcgcacc tctttcgaaa gaagtcgggg aagcggttgc   1260
aaaacgcttc catcttccag ggatacgaca aggatatggg ctcactgaga ctacatcagc   1320
tattctgatt acacccgagg gggatgataa accgggcgcg gtcggtaaag ttgttccatt   1380
ttttgaagcg aaggttgtgg atctggatac cgggaaaacg ctgggcgtta atcagagagg   1440
cgaattatgt gtcagaggac ctatgattat gtccggttat gtaaacaatc cggaagcgac   1500
caacgccttg attgacaagg atggatggct acattctgga gacatagctt actgggacga   1560
agacgaacac ttcttcatag ttgaccgctt gaagtcttta attaaataca aggatatca    1620 ggtggccccc gctgaattgg aatcgatatt gttacaacac cccaacatct cgacgcggg    1680 cgtggcaggt cttcccgacg atagcaacaa aacccgtatt gatgaagcga accagcgtgc   1740
gaccaaaatg ctgggtacca tgtatagatt tgaagaagag ctgttttac gatcccttca   1800 ggattacaaa attcaaagtg cgttgctagt accaacccta ttttcattct tcgccaaaag   1860
cactctgatt gacaaatacg atttatctaa tttacacgaa attgcttctg ggggcgcacc   1920
tctttcgaaa gaagtcgggg aagcggttgc aaaacgcttc catcttccag ggatacgaca   1980
aggatatggg ctcactgaga ctacatcagc tattctgatt acacccgagg gggatgataa   2040
accgggcgcg gtcggtaaag ttgttccatt ttttgaagcg aaggttgtgg atctggatac   2100
cgggaaaacg ctgggcgtta atcagagagg cgaattatgt gtcagaggac ctatgattat   2160
gtccggttat gtaaacaatc cggaagcgac caacgccttg attgacaagg atggatggct   2220
acattctgga gacatagctt actgggacga agacgaacac ttcttcatag ttgaccgctt   2280
gaagtcttta attaaataca aggatatca ggtggccccc gctgaattgg aatcgatatt    2340
gttacaacac cccaacatct cgacgcggg cgtggcaggt cttcccgacg atgacgccgg    2400
tgaacttccc gccgccgttg ttgttttgga gcacggaaag acgatgacgg aaaaagagat   2460
cgtggattac gtcgccagtc aagtaacaac cgcgaaaaag ttgcgcggag gagttgtgtt   2520 tgtgacgaa gtaccgaaag gtcttaccgg aaaactcgac gcaagaaaaa tcagagagat    2580
cctcataaag gccaagaagg gcggaaagtc cgagttgtaa cagctgtata cacgtgcaag   2640
ccagccagaa ctcgctcctg aagacccaga ggatctcgag caccaccacc accaccacta   2700
atgttaatta agttgggcgt tgtaatcata gtcataatca atactcctga ctgcgttagc   2760
```

```
aatttaactg tgataaacta ccgcattaaa gctattcgat gataagctgt caaacatgat    2820
aattcttgaa gacgaaaggg cctaggctga taaaacagaa tttgcctggc ggcagtagcg    2880
cggtggtccc acctgacccc atgccgaact cagaagtgaa acgccgtagc gccgatggta    2940
gtgtggggtc tccccatgcg agagtaggga actgccaggc atcaaataaa acgaaaggct    3000
cagtcgaaag actgggcctt tcgttttatc tgttgtttgt cggtgaacgc tctcctgagt    3060
aggacaaatc cgccgggagc ggatttgaac gttgcgaagc aacggcccgg agggtggcgg    3120
gcaggacgcc cgccataaac tgccaggcat caaattaagc agaaggccat cctgacggat    3180
ggcctttttg cgtttctaca aactcttttg tttattttc taaatacatt caaatatgta    3240
tccgctgagc aataactagc ataacccctt ggggcctcta aacgggtctt gagggggtttt    3300 ttgctgaaag gaggaactat atccggattg gcgaatggga cgcgccctgt agcggcgcat    3360
taagcgcggc gggtgtggtg gttacgcgca gcgtgaccgc tacacttgcc agcgccctag    3420
cgcccgctcc tttcgctttc ttcccttcct ttctcgccac gttcgccggc tttccccgtc    3480
aagctctaaa tcggggggctc cctttagggt tccgatttag tgctttacgg cacctcgacc    3540
ccaaaaaact tgattagggt gatggttcac gtagtgggcc atcgccctga tagacggttt    3600
ttcgcccttt gacgttggag tccacgttct ttaatagtgg actcttgttc caaactggaa    3660
caacactcaa ccctatctcg gtctattctt ttgatttata agggattttg ccgatttcgg    3720
cctattggtt aaaaaatgag ctgatttaac aaaaatttaa cgcgaatttt aacaaaatat    3780
taacgtttac aatttctggc ggcacgatgg catgagatta tcaaaaagga tcttaccta    3840 gatccttta aattaaaaat gaagttttaa atcaatctaa agtatatatg agtaaacttg    3900
gtctgacagt taccaatgct taatcagtga ggcacctatc tcagcgatct gtctatttcg    3960
ttcatccata gttgcctgac tccccgtcgt gtagataact acgatacggg agggcttacc    4020
atctggcccc agtgctgcaa tgataccgcg agacccacgc tcaccggctc cagatttatc    4080
agcaataaac cagccagccg gaagggccga gcgcagaagt ggtcctgcaa ctttatccgc    4140
ctccatccag tctattaatt gttgccggga agctagagta agtagttcgc cagttaatag    4200
tttgcgcaac gttgttgcca ttgctacagg catcgtggtg tcacgctcgt cgtttggtat    4260
ggcttcattc agctccggtt cccaacgatc aaggcgagtt acatgatccc ccatgttgtg    4320
caaaaaagcg gttagctcct tcggtcctcc gatcgttgtc agaagtaagt tggccgcagt    4380
gttatcactc atggttatgg cagcactgca taattctctt actgtcatgc catccgtaag    4440
atgcttttct gtgactggtg agtactcaac caagtcattc tgagaatagt gtatgcggcg    4500
accgagttgc tcttgcccgg cgtcaatacg ggataatacc gcgccacata gcagaacttt    4560
aaaagtgctc atcattggaa aacgttcttc ggggcgaaaa ctctcaagga tcttaccgct    4620
gttgagatcc agttcgatgt aacccactcg tgcacccaac tgatcttcag catcttttac    4680
tttcaccagc gtttctgggt gagcaaaaac aggaaggcaa aatgccgcaa aaaagggaat    4740
aagggcgaca cggaaatgtt gaatactcat actcttcctt tttcaatcat gaccaaaatc    4800
ccttaacgtg agttttcgtt ccactgagcg tcagaccccg tagaaaagat caaaggatct    4860
tcttgagatc ctttttttct gcgcgtaatc tgctgcttgc aaacaaaaaa accaccgcta    4920
ccagcggtgg tttgtttgcc ggatcaagag ctaccaactc tttttccgaa ggtaactggc    4980
ttcagcagag cgcagatacc aaatactgtc cttctagtgt agccgtagtt aggccaccac    5040
ttcaagaact ctgtagcacc gcctacatac ctcgctctgc taatcctgtt accagtggct    5100
gctgccagtg gcgataagtc gtgtcttacc gggttggact caagacgata gttaccggat    5160
```

-continued

```
aaggcgcagc ggtcgggctg aacgggggt tcgtgcacac agcccagctt ggagcgaacg     5220
acctacaccg aactgagata cctacagcgt gagctatgag aaagcgccac gcttcccgaa     5280
gggagaaagg cggacaggta tccggtaagc ggcagggtcg aacaggaga gcgcacgagg     5340 gagcttccag ggggaaacgc ctggtatctt tatagtcctg tcgggtttcg ccacctctga     5400
cttgagcgtc gatttttgtg atgctcgtca gggggcgga gcctatggaa aaacgccagc     5460
aacgcggcct ttttacggtt cctggccttt tgctggcctt ttgctcacat gttctttcct     5520
gcgttatccc ctgattctgt ggataaccgt attaccgcct ttgagtgagc tgataccgct     5580
cgccgcagcc gaacgaccga gcgcagcgag tcagtgagcg aggaagccgg cgataatggc     5640
ctgcttctcg ccgaaacgtt tggtggcggg accagtgacg aaggcttgag cgagggcgtg     5700
caagattccg aataccgcaa gcgacaggcc gatcatcgtc gcgctccagc gaaagcggtc     5760
ctcgccgaaa atgacccaga gcgctgccgg cacctgtcct acgagttgca tgataaagaa     5820
gacagtcata agtgcggcga cgaccggtga attgtgagcg ctcacaattc tcgtgacatc     5880
ataacgtccc gcgaaat                                                   5897
```

<210> SEQ ID NO 11
<211> LENGTH: 206
<212> TYPE: PRT
<213> ORGANISM: Homo sapiens

<400> SEQUENCE: 11

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 12
<211> LENGTH: 12
<212> TYPE: PRT
<213> ORGANISM: Artificial Sequence
<220> FEATURE:
<223> OTHER INFORMATION: substrate for the detection of botulinum

```
                                      neurotoxin activity
<220> FEATURE:
<221> NAME/KEY: misc_feature
<222> LOCATION: (1)..(1)
<223> OTHER INFORMATION: Lys at position 1 is a Lys with 5-
      carboxyfluorescein conjugated to its epsilon-amino group
      ("Lys[5-Fam]")
<220> FEATURE:
<221> NAME/KEY: misc_feature
<222> LOCATION: (11)..(11)
<223> OTHER INFORMATION: Lys at position 11 is a Lys with 4-
      (dimethylaminoazo) benzene-4-carboxyl (DABCYL) conjugated to its
      epsilon-amino group ("Lys[DABCYL]")
<220> FEATURE:
<221> NAME/KEY: misc_feature
<222> LOCATION: (12)..(12)
<223> OTHER INFORMATION: Xaa at position 12 is Nle or aminohexanoic acid

<400> SEQUENCE: 12

Lys Ile Asp Glu Ala Asn Gln Arg Ala Thr Lys Xaa
1               5                   10

<210> SEQ ID NO 13
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc_feature
<222> LOCATION: (1)..(1)
<223> OTHER INFORMATION: Lys at position 1 is a Lys with a 5-
      carboxyfluorescein conjugated to its alpha and epsilon-amino
      groups ("5-Fam-Lys[5-Fam]")
<220> FEATURE:
<221> NAME/KEY: misc_feature
<222> LOCATION: (11)..(11)
<223> OTHER INFORMATION: Lys at position 11 is a Lys with 4-
      (dimethylaminoazo) benzene-4-carboxyl (DABCYL) conjugated to its
      epsilon-amino group ("Lys[DABCYL]")
<220> FEATURE:
<221> NAME/KEY: misc_feature
<222> LOCATION: (12)..(12)
<223> OTHER INFORMATION: Xaa at position 12 is Nle or aminohexanoic acid

<400> SEQUENCE: 13

Lys Ile Asp Glu Ala Asn Gln Arg Ala Thr Lys Xaa
1               5                   10

<210> SEQ ID NO 14
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc_feature
<222> LOCATION: (1)..(1)
<223> OTHER INFORMATION: Lys at position 1 is a Lys with a 5-
      carboxyfluorescein conjugated to its alpha-amino groups
      ("5-Fam-Lys")
<220> FEATURE:
<221> NAME/KEY: misc_feature
<222> LOCATION: (11)..(11)
<223> OTHER INFORMATION: Lys at position 11 is a Lys with 4-
      (dimethylaminoazo) benzene-4-carboxyl (DABCYL) conjugated to its
      epsilon-amino group ("Lys[DABCYL]")
<220> FEATURE:
<221> NAME/KEY: misc_feature
<222> LOCATION: (12)..(12)
<223> OTHER INFORMATION: Leu at position 12 is Nle

<400> SEQUENCE: 14
```

Lys Ile Asp Glu Ala Asn Gln Arg Ala Thr Lys Leu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc_feature
<222> LOCATION: (1)..(1)
<223> OTHER INFORMATION: Lys at position 1 is a Lys with a 5-
      carboxyfluorescein conjugated to its alpha and epsilon-amino
      groups ("5-Fam-Lys[5-Fam]")
<220> FEATURE:
<221> NAME/KEY: misc_feature
<222> LOCATION: (11)..(11)
<223> OTHER INFORMATION: Lys at position 11 is a Lys with 4-
      (dimethylaminoazo) benzene-4-carboxyl (DABCYL) conjugated to its
      epsilon-amino group ("Lys[DABCYL]")
<220> FEATURE:
<221> NAME/KEY: misc_feature
<222> LOCATION: (12)..(12)
<223> OTHER INFORMATION: Leu at position 12 is Nle

<400> SEQUENCE: 15

Lys Ile Asp Glu Ala Asn Gln Glu Leu Thr Lys Leu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc_feature
<222> LOCATION: (12)..(12)
<223> OTHER INFORMATION: Leu at position 12 is Nle

<400> SEQUENCE: 16

Lys Ile Asp Glu Ala Asn Gln Arg Ala Thr Lys Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc_feature
<222> LOCATION: (1)..(1)
<223> OTHER INFORMATION: Lys at position 1 is a Lys with a 5-
      carboxyfluorescein conjugated to its alpha-amino groups
      ("5-Fam-Lys")
<220> FEATURE:
<221> NAME/KEY: misc_feature
<222> LOCATION: (11)..(11)
<223> OTHER INFORMATION: Lys at position 11 is a Lys with 4-
      (dimethylaminoazo) benzene-4-carboxyl (DABCYL) conjugated to its
      epsilon-amino group ("Lys[DABCYL]")
<220> FEATURE:
<221> NAME/KEY: misc_feature
<222> LOCATION: (12)..(12)
<223> OTHER INFORMATION: Leu at position 12 is Nle

<400> SEQUENCE: 17

Lys Ile Asn Glu Ala Asn Gln Glu Leu Thr Lys Leu
1               5                   10

```
<210> SEQ ID NO 18
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc
<222> LOCATION: (1)..(1)
<223> OTHER INFORMATION: Lys at position 1 is a Lys with 5-
      carboxyfluorescein conjugated to its epsilon-amino group
      ("Lys[5-Fam]")
<220> FEATURE:
<221> NAME/KEY: misc
<222> LOCATION: (11)..(11)
<223> OTHER INFORMATION: Lys at position 11 is a Lys with 4-
      (dimethylaminoazo) benzene-4-carboxyl (DABCYL) conjugated to its
      epsilon-amino group ("Lys[DABCYL]")
<220> FEATURE:
<221> NAME/KEY: misc
<222> LOCATION: (12)..(12)
<223> OTHER INFORMATION: Leu at position 12 is Nle

<400> SEQUENCE: 18

Lys Ile Asn Glu Ala Asn Gln Glu Leu Thr Lys Leu
1               5                   10

<210> SEQ ID NO 19
<211> LENGTH: 13
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc_feature
<222> LOCATION: (1)..(1)
<223> OTHER INFORMATION: Thr at position 1 is a Thr with 5-
      carboxyfluorescein conjugated to its N-terminal ("5-Fam-Thr")
<220> FEATURE:
<221> NAME/KEY: misc_feature
<222> LOCATION: (12)..(12)
<223> OTHER INFORMATION: Lys at position 12 is a Lys with 4-
      (dimethylaminoazo) benzene-4-carboxyl (DABCYL) conjugated to its
      epsilon-amino group ("Lys[DABCYL]")
<220> FEATURE:
<221> NAME/KEY: misc_feature
<222> LOCATION: (13)..(13)
<223> OTHER INFORMATION: Xaa at position 13 is 6-aminohexanoic acid

<400> SEQUENCE: 19

Thr Arg Ile Asp Glu Ala Asn Gln Arg Ala Thr Lys Xaa
1               5                   10

<210> SEQ ID NO 20
<211> LENGTH: 12
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc_feature
<222> LOCATION: (1)..(1)
<223> OTHER INFORMATION: Thr at position 1 is a Thr with 5-
      carboxyfluorescein conjugated to its N-terminal ("5-Fam-Thr")
<220> FEATURE:
<221> NAME/KEY: misc_feature
<222> LOCATION: (12)..(12)
<223> OTHER INFORMATION: Lys at position 12 is a Lys with 4-
      (dimethylaminoazo) benzene-4-carboxyl (DABCYL) conjugated to its
      epsilon-amino group ("Lys[DABCYL]")
```

```
<400> SEQUENCE: 20

Thr Arg Ile Asp Glu Ala Asn Gln Arg Ala Thr Lys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc_feature
<222> LOCATION: (1)..(1)
<223> OTHER INFORMATION: Thr at position 1 is a Thr with 5-
      carboxyfluorescein conjugated to its N-terminal ("5-Fam-Thr")
<220> FEATURE:
<221> NAME/KEY: misc_feature
<222> LOCATION: (12)..(12)
<223> OTHER INFORMATION: Lys at position 12 is a Lys with 4-
      (dimethylaminoazo) benzene-4-carboxyl (DABCYL) conjugated to its
      epsilon-amino group ("Lys[DABCYL]")
<220> FEATURE:
<221> NAME/KEY: misc_feature
<222> LOCATION: (13)..(13)
<223> OTHER INFORMATION: Leu at position 13 is Nle

<400> SEQUENCE: 21

Thr Arg Ile Asp Glu Ala Asn Gln Arg Ala Thr Lys Leu
1               5                   10

<210> SEQ ID NO 22
<211> LENGTH: 13
<212> TYPE: PRT
<213> ORGANISM: Artificial Sequence
<220> FEATURE:
<223> OTHER INFORMATION: substrate for the detection of botulinum
      neurotoxin activity
<220> FEATURE:
<221> NAME/KEY: misc_feature
<222> LOCATION: (1)..(1)
<223> OTHER INFORMATION: Thr at position 1 is a Thr with 4-
      Methylumbelliferone conjugated to its N-terminal ("4-MU")
<220> FEATURE:
<221> NAME/KEY: misc_feature
<222> LOCATION: (12)..(12)
<223> OTHER INFORMATION: Lys at position 12 is a Lys with 4-
      (dimethylaminoazo) benzene-4-carboxyl (DABCYL) conjugated to its
      epsilon-amino group ("Lys[DABCYL]")
<220> FEATURE:
<221> NAME/KEY: misc_feature
<222> LOCATION: (13)..(13)
<223> OTHER INFORMATION: Leu at position 13 is Nle

<400> SEQUENCE: 22

Thr Arg Ile Asp Glu Ala Asn Gln Arg Ala Thr Lys Leu
1               5                   10
```

METHODS FOR DETECTION OF BOTULINUM NEUROTOXIN

PRIORITY CLAIM

This application claims the benefit of U.S. Provisional Patent Application Ser. No. 60/942,199, filed Jun. 5, 2007, which is incorporated herein by reference.

GOVERNMENT INTEREST

The present invention was supported by National Institutes of Health grant AI-65359. The government may have certain rights in the present invention.

BACKGROUND

Botulinum neurotoxins (BoNTs) are important medical agents, used to treat dystonias, blepharospasms, hyperhidrosis and other neurological diseases. However, BoNTs also represent the most toxic substances known and their potential abuse as a threat agent is feared (Arnon 2001; Wein 2005). The detection of Botulinum neurotoxin (BoNT) in complex samples such as foods or clinical specimens represents an analytical challenge. The current "gold standard" in the art for detecting BoNT is the mouse toxicity assay, which can detect as little as 10 pg BoNT (Ferreira 2003). However, BoNT can be lethal to humans in systemic doses as low as 1 to 2 ng/Kg body weight (Arnon 2001). Therefore, there is a need in the art for more sensitive assays for detecting the presence of BoNT in a sample.

SUMMARY

In certain embodiments, methods are provided for detection of BoNT in complex biological samples with high sensitivity and specificity. In certain of these embodiments, the methods are based on specific affinity enrichment of a target toxin or target enzyme ("target") onto a solid support followed by fluorometric or luminescent readout. In certain of these embodiments, the assays have a sensitivity of at least about 0.5 femtograms target per one mL sample or about 300 target molecules per sample. In certain of these embodiments, the solid support is a bead matrix that contains immobilized, anti-enzyme-specific antibodies and/or anti-toxin-specific antibodies. In other embodiments, capture or immobilization of the target toxin or enzyme such that the toxin or enzyme's activity on its substrate is accelerated. In certain embodiments, capture or immobilization of the target toxin or enzyme is achieved without resulting in inactivation or reduction of the target activity on its substrate. For example, antibodies may be BoNT-specific antibodies that capture BoNT but do not inactivate BoNT-specific enzymatic activity. Also, antibodies may be BoNT-specific antibodies that capture BoNT such that the BoNT activity is accelerated.

In certain of these embodiments, the fluorometric readout is based on specific cleavage of a fluorogenic substrate. For example, BoNT-specific cleavage of a fluorogenic BoNT substrate such as the SNAPtide described in U.S. Pat. No. 6,504,006 as well as other coumarin derivatives are useful in certain embodiments. Additional suitable substrates include various soluble NSF attachment protein receptor (SNARE), or one or more fluorogenic toxin or enzyme peptide substrate.

The methods provided herein may be used to detect BoNT type A, B, C, D, E, F, and/or G, or their subtypes. In certain embodiments, methods are provided for detection of BoNT serotypes including subtypes with attomolar sensitivity. The assays include use of a BoNT serotype A assay with a large immuno-sorbent surface area (BoNT/A ALISSA) that has attomolar sensitivity in biological samples such as complex samples, serum and liquid foods.

In other embodiments, luminescent based readout assays are provided for detection of BoNT. The methods include use of bioluminescent BoNT/A substrates including genetically engineered variants of recombinant luciferase proteins. In certain embodiments, bioluminescent assays include use of luminescent proteins able to emit light at multiple wavelength for multiplexed simultaneous detection of one or more serotype.

In certain embodiments, the methods and assays include development and use of novel fluorogenic or bioluminescent substrates for toxin or enzyme detection. Such novel substrates include those having resistance to non-BoNT proteases while remaining cleavable by the target toxin or enzyme.

The methods and assays provided are broadly useful and as such may be used to detect a wide variety of toxins and/or other enzymes such as anthrax lethal factor, human chitinases (e.g. CHIT1 or AMCase) and proteases such as fungal protease Pep1 and Pep2 from *Aspergillus fumigatus*. The ALISSA methods may be expanded for use in detection of any toxin or enzyme including all BoNT serotypes.

The systems, methods and kits provided herein may be used to detect and/or measure toxin or enzyme levels in a variety of samples. In certain embodiments, the methods may be used to measure toxin or enzyme distribution in systemic circulation, in a biological fluid sample, cell, tissue and/or organ of an animal or human. The sensitivity, specificity, speed and simplicity of the methods provided herein are particularly useful for diagnostic, biodefense and pharmacological applications.

In addition to the exemplary embodiments described above, further embodiments and aspects will become apparent by reference to the drawings and by study of the following descriptions.

BRIEF DESCRIPTION OF DRAWINGS

FIG. 1 shows (A) Synthesis of the immuno-affinity matrix for BoNT enrichment. Protein A sepharose beads are coupled to affinity purified anti-BoNT antibodies. The FC domain of the antibodies is cross-linked to the protein A using disuccinimidyl suberate (DSS). Non-cross-linked antibodies are removed through stringent washing. (B) Cleavage of fluorigenic substrate by immuno-affinity enrichment of BoNT/A.

FIG. 4 shows a determination of assay performance. (A) Detection of BoNT/A from two different commercial sources, Metabiologics ([1]) and the List BioLabs ([2]) in serum spiked with serially diluted toxin. "pre-act" indicates toxin pre-activation in 5 mM DTT. (B) Detection of BoNT/A in representative complex samples. The samples were spiked with undiluted human serum, carrot juice, reconstituted non-fat powdered milk, fresh milk and GP-diluent.

FIGS. 5C and 5D illustrate the hydrolysis of SNAPtide by BoNT/A by a linear relationship between the reciprocal substrate concentration and the activity of the enzyme in bead-based ALISSA and bead-free assays, respectively.

FIG. 7 shows a schematic of one embodiment of a BoNT ALISSA.

FIG. 11 shows schematic representations of two strategies for bioluminescent detection system. (A) shows an assay comprising a Dual Chamber system; (B) shows an assay comprising a Single Chamber system. Identifiers "A" and "B" represent non-FFL protein domains having well characterized dimerization properties such as Glutathione S-transferase (GST) and glutathione or IgG FC-region and protein A.

FIG. 12 shows (A) an exemplary schematic of a synthesis scheme for constructing recombinant overlapping split FFL having a SNAP25-sequence insert (SEQ ID NO: 1). As depicted, two PCR products are generated using a yeast plasmid (pGAL-FFL) as a template and then cloned subsequently into the same pETBlue-2 vector. The BoNT/A leavage site for SNAP25 (amino acid residues 187 to 206; SEQ ID NO: 6) is embedded into the sequence via synthetic primers (SEQ ID NO: 7 and 8) using a codon-optimized sequence for *E. coli*. Similar synthesis schemes are employed for constructing split FFL fusion proteins for targeted SNARE sequence of other BoNT serotypes. (B) shows restriction analysis of the intermediate plasmid depicted in (A) (plasmid "1"; SEQ ID NO: 9) and the final product (plasmid "2"; SEQ ID NO: 10). The identifier "1" is the uncut pETBlue-2 FFL[1-475] vector; "1 cut" is "1" cut with NcoI and KpnI; "2" is the uncut final product pETBlue-2FFL[1-475]-SNAP-FFL[265-550] and "2 cut" is the "2" cleaved with NcoI and PvuII.

FIG. 13 shows the nucleic acid sequence of FFL1-478SNAP25FFL265-550 (SEQ ID NO:3) is depicted. In this embodiment of an overlapping split FFL having a SNAP25 sequence insert, nucleic acids encoding amino acids 1 through 478 of FFL is included in the first FFL segment. The corresponding SNAP25 sequences with the BoNT/A cleavage site are indicated in bold and underlined text. The hexahistidine tag is indicated in bold and italic text.

FIG. 14 shows the amino acid sequence of FFL1-478SNAP25FFL265-550 (SEQ ID NO:4) is depicted. In this embodiment of an overlapping split FFL having a SNAP25 sequence insert, amino acids 1 through 478 of FFL is included in the first FFL segment. The corresponding SNAP25 sequences with the BoNT/A cleavage site are indicated in bold and underlined text. The hexahistidine tag is indicated in bold and italic text.

FIG. 15 shows the complete amino acid sequence of human SNAP25 (SEQ ID NO: 11; Swissprot Accession #P60880). The BoNT/A cleavage and recognition site (SEQ ID NO: 2) is indicated in bold and underlined text.

DETAILED DESCRIPTION

Figure 2:
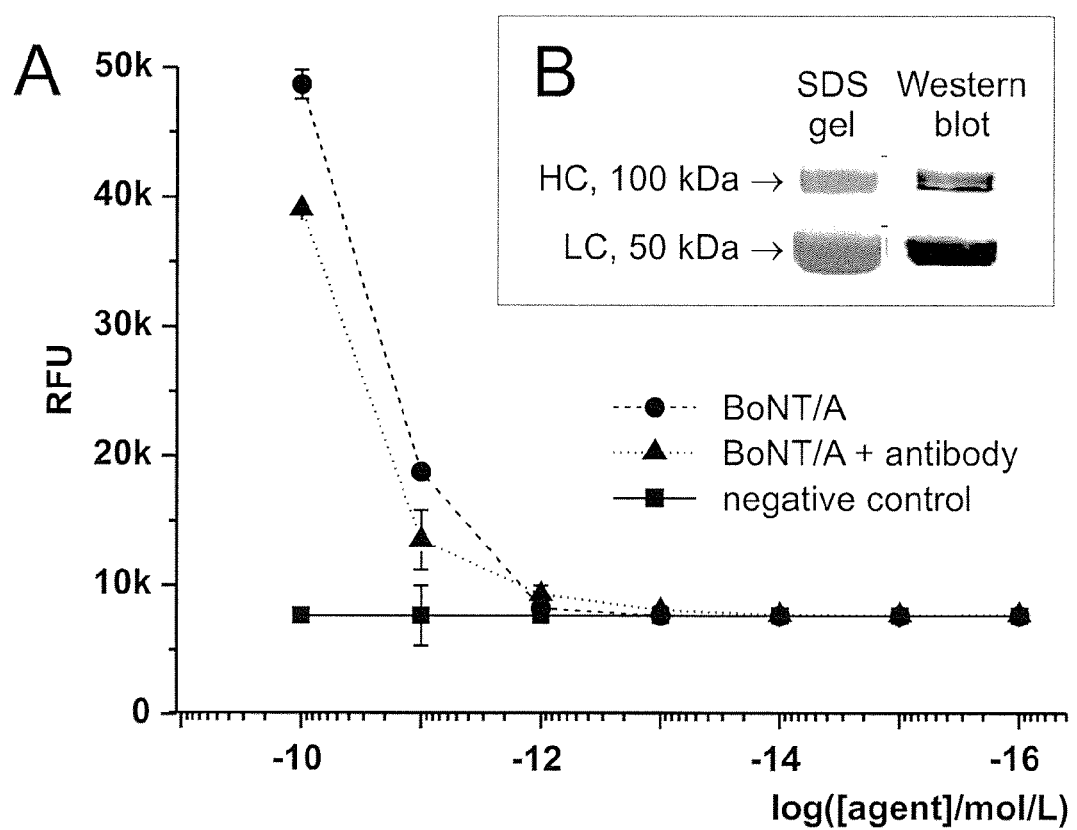
FIG. 2 shows (A) Immobilized polyclonal rabbit antibody does not significantly inhibit specific proteolytic activity of BoNT/A and (B) Western blot analysis of BoNT/A using anti-*Clostridium botulinum* A toxoid antibodies. The antibody recognized both heavy (H) and light (L) chain of the toxin.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Natural BoNT resides within ~300, 500 or 900-kDa protein complexes together with other non-toxic components, the neurotoxin associated proteins (NAPs) (Sakaguchi 1982; Chen 1998; Sharma 2003; Melling 1988; Zhang 2003; Aoki 2001). Several structurally distinct serotypes of BoNT (types A to G) have been discovered. BoNT Type A (BoNT/A) is most prevalent in the Western United States (Smith 1978) and is causatively involved in approximately 60% of the IB cases in California (the rest being mostly attributed to type B) (Amon 2001). The toxin itself is a 150-kDa zinc-binding metalloprotease that, following expression, is endogenously cleaved into a 100-kDa heavy and a 50-kDa light chain connected by a reducible disulphide bond (Schiavo 2000) and by a belt-like extension of the heavy chain that loops around the light chain (Lacy 1998). The catalytic site is located on the light chain (Kurazono 1992). Reduction of the chain-bridging disulphide bond exposes the catalytic site and enhances its activity (Lacy 1998), also referred to as "activation" of the toxin by some authors and toxin manufacturers (Cai 1999; Cai 2001). The potency of BoNT results from its ability to cleave on or more of the three SNARE proteins involved in fusing acetylcholine-containing synaptic vesicles with terminal motor neurons membrane, triggering muscle contraction (Shiavo 2000).

Detection of low levels of BoNT in a sample using prior art methods is difficult. However, due to the enormous potency of the toxin, which can be lethal for humans in systemic doses of 1 to 2 ng/Kg body weight (Arnon 2001), these low levels can be extremely dangerous. For example, in infant botulism (IB), a condition in which a baby's intestines have become colonized by toxin-secreting *Clostridium botulinum* bacteria, it is possible to detect BoNT in stool samples (Arnon 2006). However, attempts to diagnose IB serologically via detection of BoNT in the blood have been deemed unreliable (Schantz 1992). Nevertheless, the systemic presence of the toxin in IB cannot be disputed, because of its apparent quick distribution throughout the infant's entire body, by which it efficiently shuts down motor neurons distant from the intestinal source. The resulting symptoms can include complete paralysis and respiratory failure.

The definite diagnosis of botulism requires detection of BoNTs in clinical specimens. Most commonly used and relied on is the life mouse assay. This assay can detect as little as 10 pg BoNT (Ferreira 2003). In the life mouse assay, mice are injected intraperitoneally (i.p.) with 0.5 mL/mouse of sample, treated with type A or B antitoxin, and observed for signs of botulism or death, typically over a 48 hour period. Toxicity is expressed by the number of hours until death (Kautter 1977; Sharma 2006). As in many animal experiments, the results of the mouse assay may vary. Four- to five-fold differences in response to a given dose are typical (Sugiyama 1980). Other and generally faster methods for BoNT detection include use of fluorescence resonance energy transfer (FRET) substrates for BoNT (U.S. Pat. No. 6,504,006), various enzyme-linked immunosorbent assays (ELISAs) (Sharma 2006), Enzyme-amplified protein micro arrays with a "fluidic renewable surface fluorescence immunoassay" (Varnum 2006), mass spectrometric assays (Barr 2005; Kalb 2005; Boyer 2005; Kalb 2006), immuno-PCR detection (Chao 2004), and recently, a real-time PCR-based assay that utilizes reporter DNA-filled liposomes which bind to immobilized BoNT/A via gangliosides (Mason 2006a; Mason 2006b). Reported detection limits and sample types for these various methods are summarized in Table 1. Except for the PCR-based assays, most assays are not well suited to provide the desired detection of less than 1 pg/mL BoNT in a complex sample. By approximation, 1 pg/mL corresponds to the lethal concentration under presumed equal distribution throughout the human body.

TABLE 1

Reported performance of existing Botulinum toxin assays

| Test method | Demonstrated for Sample Type | Sensitivity (fg/mL) | Assay Time |
|---|---|---|---|
| Mass spectrometry (Endopep-MS)[22-25] | milk, serum, stool extract | 320,000 | <4 hrs |
| Enzyme-linked immunosorbent assays (ELISA)[19] | liquid and solid foods, serum | 60,000 | 6-8 hrs |
| ELISA-HRP[29] | therapeutic preparations | 9,000 | 4-6 hrs |
| Mouse assay (gold standard)[18] | foods, serum, stool | ~6,000 | typically 48 hrs |
| Enzyme-amplified protein microarray and fluidic renewable surface fluorescence immunoassay[21] | blood, plasma | 1,400 | <10 min. per measurement |
| Immuno-PCR[26] | carbonate buffer | 50 | 4-6 hrs |
| Immuno-PCR with ganglioside-mediated liposome capture[27,28] | deionized water | 0.02 | 6 hrs |

Provided herein is a simple laboratory method for detecting the activity of a toxin or enzyme that utilizes common lab equipment and commercially available reagents, and is therefore expected to be reproducible by any reasonably well equipped biological laboratory. This method is referred to herein as a Assay with a Large Immuno-sorbent Surface Area (ALISSA). The examples set forth herein provide a detailed protocol for the ALISSA, as well as an analysis of the effect of various experimental parameters on the assay. In certain embodiments, the ALISSA is employed for the detection of botulinum toxin A (BoNT/A). For example, the exemplary experimental results disclosed herein show that the assay can detect less than 0.5 fg of BoNT/A holotoxin in 1 mL serum, milk, or GP-diluent. Based on these results, the ALISSA is at least about 32,000-fold more sensitive than the life mouse assay and about 160.000-fold more sensitive than the Enzyme-linked Immunosorbent Assay (ELISA). In certain embodiments, the turnaround time for the ALISSA is one to two hours, which is significantly faster than the life mouse assay (~48 hours) and faster than ELISA (~3 hours). The exemplary experimental results obtained herein were obtained with BoNT type A (BoNT/A), but could be applied just as easily to other BoNT serotypes or other toxins as well as enzymes.

The ALISSA avoids interference with other sample components by using a highly specific affinity matrix and exploiting the natural catalytic activity of the toxin or enzyme ("target") with a target-specific substrate. Both of these steps amplify the signal via localized enrichment of the toxin and enzymatic conversion of multiple substrate molecules per toxin molecule.

In certain embodiments, ALISSA consists of two main steps: 1) capture and enrichment of toxin or enzyme on a bead-based immuno-affinity matrix and removal of unspecific binding molecules, and 2) determination of the enzymatic activity of the immobilized toxin or enzyme based on cleavage of a specific fluorigenic or bioluminescent substrate. In certain embodiments, the immuno-affinity matrix consists of protein-A conjugated sepharose beads coupled and cross-linked to anti-toxin or anti-enzyme antibodies. For example, the immunoaffinity matrix can consist of protein-A conjugated sepharose beads coupled and cross-linked to anti-BoNT antibodies. The immunosorbent support provided herein can be comprised of either loose beads or one or more fixed column.

As used herein, the term "target" when used to refer to a toxin or enzyme, is used to refer to any chemical, biochemical or biological species or compound that is known or referred to in the art as a toxin or an enzyme. A target toxin or target enzyme includes those compounds having proteolytic, catalytic or enzymatic activity. A target toxin or target enzyme includes those compounds able to modify a substrate so as to alter or change the substrate's chemical structure or apparent structure or activity. For example, a botulinum neurotoxin type A is a "target" toxin that has proteolytic activity and is able to cleave its specific substrates. As another example, a chitinase is a "target" enzyme that has enzymatic activity.

As used herein, the term "substrate" is used to refer to any chemical, biochemical or biological species or compound that complexes with, reacts, with, is capable of being modified by, or otherwise interacts with a toxin or enzyme having bioactivity. For example, a botulinum type toxin is a protease able to enzymatically cleave specific protein substrates such as synaptic membrane proteins, SNARE proteins or SNAP-25 proteins. As another example, a chitinase substrate interacts with a chitinase enzyme such as endochitinase or exochitinase.

As used herein, the term "fluorogenic substrate", and "fluorophore" may be used interchangeably to describe a substrate that is hydrolyzed by or otherwise reacted with a target toxin upon contact therewith, producing a complex, product or other derivative thereof which liberates fluorescence upon excitation by a suitable light source.

As used herein the term "bioluminescent substrate", "luminescent substrate", and "luminogenic" protein may be used interchangeably to describe a substrate that is activated by or otherwise interacts or reacts with a target toxin upon contact therewith, producing a complex, product, or other derivative thereof which emits light at distinct wavelengths suitable for detection as desired.

In accordance with the method of the invention, one or more sample from a source suspected of containing a toxin is obtained and then contacted with a substrate composition comprising a toxin substrate, such as a fluorogenic or luminogenic substrate or a mixture thereof, for a period of time and under conditions sufficient to permit the toxin to react with the toxin substrate to cause a measurable change in a property such as fluorescence or light emission, or the resulting reaction product.

In general, the toxin or enzyme contained in the sample is first captured on an enrichment matrix such as a bead-based immuno-affinity matrix containing immobilized anti-toxin specific antibodies. Immobilization of the antibodies to the matrix can be by a variety of methods, including, for example by covalent crosslinking of the Fc region of the antibody to the beads. Once captured, the toxin or enzyme molecules retain enzymatic function and specificity for its substrate.

The natural substrate of BoNT/A is the 25-kDa synaptosomal-associated protein (SNAP 25), which it cleaves at distinct sites, thereby preventing the release of neurotransmitters (Schiavo 1993a; Schiavo 1993b). In those embodiments wherein BoNT/A is being detected, the enzymatic activity of BoNT/A may be utilized to cleave the fluorigenic substrate SNAPtide, which is a synthetic, commercially available, 13-amino acid peptide that contains the native SNAP-25 cleavage site for BoNT/A (U.S. Pat. No. 6,504,006). In those embodiments wherein a BoNT type other than type A is being detected, the fluorogenic substrate may be any substrate that is specifically cleaved by the BoNT type being detected. In those embodiments were a different class or type of toxin other than a BoNT is being detected, the substrate may be any substrate that is specifically cleaved or catalyzed by the toxin being detected.

The present invention provides a method for detecting toxin or enzyme which avoids interference with other sample components by use of high toxin-specific affinity matrix and toxin-specific substrates. For example, use of a high affinity BoNT/A specific matrix and a BoNT/A-specific substrate reduces or avoids interference by other components present within a sample thus amplifying the signal and increasing the assay's sensitivity. Use of a toxin-specific substrate also exploits the natural proteolytic activity of the toxin. Signal amplification is achieved by localized enrichment of the toxin and through enzymatic conversion of substrate molecules. In certain embodiments, the capture matrix is designed to stably enrich the toxin while retaining enzymatic activity. The capture matrix may also purify toxin from non-specific components or proteases present within the sample. Use of a beaded protein A matrix to bind anti-toxin antibodies via FC-region allows orientation of the antibody binding domains away from the bead surface and into the surrounding fluid. This augments and provides increased accessibility for toxin molecules. Use of a bead-based assays also allows for wash steps that diminish interference by other proteases. The present invention provides a considerably faster and more sensitive method for detecting toxin and its activity.

Detection of all BoNT serotypes including subtypes is also achieved utilizing novel fluorogenic or luminogenic substrates. The botulinum neurotoxins cleave a variety of vertebral SNARE (Soluble NSF attachment protein receptor) in vivo and in vitro. While some fluorogenic BoNT substrates based on natural SNARE sequence are known (Schmidt 2003), the possible interference by sterically demanding fluorophore or quencher moieties on the catalytic cleavage reaction of such fluorogenic peptides remains a concern. The present invention provides novel substrates that achieve higher chemical stability and comparable or superior sensitivity as compared to prior peptides. Preferably, fluorophore substrates that allow for efficient cleavable fluorophore and quencher combinations are selected for use in the ALISSA assay. Generally, fluorophore and quencher require proximities of about 10 nm or less to allow sufficient FRET-mediated quenching. Closer distances are also preferred to reduce background fluorescence from the quenched substrates. In certain embodiments, use of bioluminescent substrates to allow for luminescent BoNT detection may be desired. Luminescent based assays can reduce or omit the requirement for a light source and provide greater signal-to-noise ratios. Bioluminescent light in particular, can be detected using less complex means such as with miniaturized photomultipliers or microscopic avalanche photodiodes. Furthermore, potential interference from background fluorescence due to inert components of a microfluidic device are alleviated.

Novel fluorogenic substrates for BoNT serotypes such as serotypes A to G are designed through use of peptide libraries having proteinogenic and as well as non-proteinogenic amino acids. Preferably, those substrates having resistance to non-BoNT proteases are selected for use with the ALISSA or other immobilized antibody matrix based assay. More preferably, substrates designed so as to be more specifically and readily cleaved by BoNT are also provided. Thus, the present invention includes methods for detecting BoNT of all serotypes and subtypes in one or more biological sample, in vitro or in vivo using affinity capture of BoNT on microscopic beads coated with antibodies specific to the toxin. The antibody captured toxin retains its metalloprotease activity. The method includes use of a reporter molecule such as a fluorogenic or bioluminescent substrate that is cleavable by one or more molecules of the captured BoNT. Fluorescence is then detected using a handheld ultraviolet (UV) light, a fluorescence excitation and/or detecting tool, device or any suitable commercially available fluorometer. Luminescence is detected using any suitable commercially available luminometer.

The present invention provides an inexpensive, robust method providing high analytical specificity and attomolar sensitivity for detection of toxin or enzyme in complex biological samples. The ALISSA will improve the diagnosis of botulism and other toxins significantly and could serve to protect humans in biomedical and bio-defense scenarios. The method may also be applied for the routine testing of foods and for forensic investigation.

The present invention also provides methods for identifying novel fluorogenic and luminogenic substrates useful for detecting the presence and/or activity of a toxin or enzyme. Such toxin-specific substrates are useful for detecting, identifying and/or assaying for the presence or activity of a toxin or enzyme in a sample at attomolar levels of sensitivity. For example, it is known that botulinum neurotoxins cleave a variety of SNARE proteins. Sequences of natural SNARE proteins have been used to produce fluorogenic BoNT peptide substrates. Such methods generally entail use of terminal fluorophore and quencher molecule pairing (fluorescence through resonance energy transfer), or FRET moieties. It is difficult, however, to predict the effect that sterically demanding fluorophore or quencher moieties will have on the ability of the toxin to effectively cleave the resulting fluorophore modified substrate molecule. The present invention provides novel fluorogenic substrate peptides by employing synthetic peptide libraries to screen for those substrates that readily contain fluorophore and quencher combinations.

The present invention also provides methods for the identification of novel luminogenic protein substrates. Using recombinant methodology, genetically engineered variants of recombinant luciferase proteins that become activated by specific BoNT cleavage reactions are provided. Thus, the methods provide luminescent substrates specific for all serotypes and subtypes of botulinum toxin.

The present invention employs two general approaches to exploiting bioluminescence for identifying novel bioactive luminogenic substrates. The first includes use of complementation of inactive luciferase fragments to restore active luciferase molecules. The second includes use of specific reactions that release D-luciferin as a substrate for firefly luciferase (FFL from *Photinus pyralis*). Complementation assays for luciferase are described by Paulmurugan et al., "Combinatorial library screening for developing an improved split-firefly luciferase fragment-assisted complementation system for studying protein-protein interactions," *Anal Chem.*, 79:2346-2353 (2007); and Paulmurugan et al., "Firefly luciferase enzyme fragment complementation for imaging in cells and living animals," *Anal. Chem.* 77:1295-1302 (2005). Using described complementation assays, split luciferase constructs are designed for use in detecting the presence of specific enzymatic activity. Whereas such constructs are inactive when in their fused, non cleaved state, upon interacting with a target toxin such as BoNT, the proteolytic activity of the toxin cleaves the luminogenic substrate thereby releasing a detectable luminescent signal. Luminogenic substrates for all toxins and enzymes as well as the seven serotypes (A to G) of BoNT can be detected by such specific substrates.

The novel substrates can also be obtained by the usual methods of solid-phase synthesis according to the Merrifield method on an automatic synthesizer such as, for example, the 431A synthesizer from Applied Biosystems. The chemistry used corresponds to Fmoc technology and protection of the side chains allowing cleavage thereof with trifluoroacetic acid, as described by E. Atherton and R. C. Sheppard (1989) in "Solid Phase Peptide Synthesis: a practical approach, IRL Press, Oxford".

EXAMPLES

Example 1

Materials and Methods

The pure 150 kDa BoNT A toxin (holotoxin) was purchased from two distinct commercial sources: from the List of Biological Laboratories (Campbell, Calif.) and Metabiologics Inc. (Madison, Wis.). BoNT/A complex, IP and IV mouse assays in 50 mM citrate buffer, pH 5.5 was received from Dr E. Jonson's laboratory, Food Research Institute of the University of Wisconsin-Madison. The intact BoNT/A toxin complex and BoNT/A toxoid were from MetaBiologics. SNAPtide™ (FITC/DABCYL), synthetic peptide containing the native cleavage site for Botulinum toxin type A and SNAPtide®, unquenched calibration peptide for SNAPtide™ (FITC/DABCYL), were purchased from the List of Biological Laboratories. The latter contains the FITC bound to the N-terminal cleaved fragment of SNAPtide; it was used as a calibrant to convert fluorescence intensity units to changes in the molar ratio of peptide cleavage product. All types of BoNT/A toxin were from Hall A, *Clostridium botulinum* producing strain. In one example, the BoNT/A subtype used was A1. Toxin activities for the holotoxin and the complex were $2.1\times10^8$ MLD$_{50}$/mg and $3.6\times10^7$ MLD$_{50}$/mg, respectively, according to Metabiologics.

In certain embodiments, the fluorogenic peptide is SNAPtide (U.S. Pat. No. 6,504,006) which is a molecular derivative of SNAP25, the natural substrate of BoNT/A. SNAPtide is cleaved by BoNT/A between a fluorophore and a quencher (FRET pair) releasing unquenched fluorophore. The SNAPtide contains a conjugated fluorescein thiocarbamoyl (FITC) quenched by a 4-(dimethylaminoazo) benzene-4-carboxyl (DABCYL)-moiety. The fluorogenic peptide SNAPtide (FITC/DABCYL, product #521) and the unquenched calibration peptide, containing an N-terminally FITC-labeled fragment of SNAPtide (product #528, synthetic, but sequence identical to the BoNT/A cleaved product), were from List Biological Laboratories. In other embodiments, the substrate comprises a SNAPtide peptide wherein the N-terminal fluorescein isothiocyanate was replaced with 5-carboxy fluorescein. Such labeling improves stability of the substrate. In certain embodiments, 4-methylumbelliferone labeling was utilized allowing use of a substrate having blue fluorescence.

Affinity purified Rabbit polyclonal to *Clostridium botulinum* A Toxoid (formaldehyde inactivated Type A Neurotoxin (*C. botulinum*) antibodies were purchased from Abcam (Cambridge, UK). Purified rabbit IgG was from (ICN Biomedical Inc., Aurora, Ohio), Seize® X Protein A Immunoprecipitation Kit was from Pierce (Rockford, Ill.), Trypsin was from Promega, Fetal Bovine Serum was from Invitrogen (Carlsbad, Calif.). Human serum was from Sigma (cat. #H4522) and carrot juice was from Bolthouse Farms (Organics, 100% carrot juice, 1 liter bottle). Other reagents were from Sigma unless indicated. Concentrations of the toxins were determined according to the extinction coefficient (Ahmed et al., 2001) or by Bicinchoninic Acid (BCA, Pierce) Protein Assay, a Micro Assay for dilute protein solutions, with BSA as standard. Both methods gave the same result. The product was exclusively the dichain form of the toxin as judged by the 12% sodium dodecyl sulfate-polyacrylamide gel electrophoresis at room temperature (25° C.) under reducing conditions. Gels were analyzed by Western Blot using Rabbit polyclonal to *Clostridium botulinum* A Toxoid (Abcam). The bands on the gels were visualized by Coomassie Blue or Silver staining or with the SimplyBlue SafeStain kit from Invitrogen (Carlsbad, Calif.).

Example 2

Assay Design

Preparation of the Immunomatrix.

Figure 3:
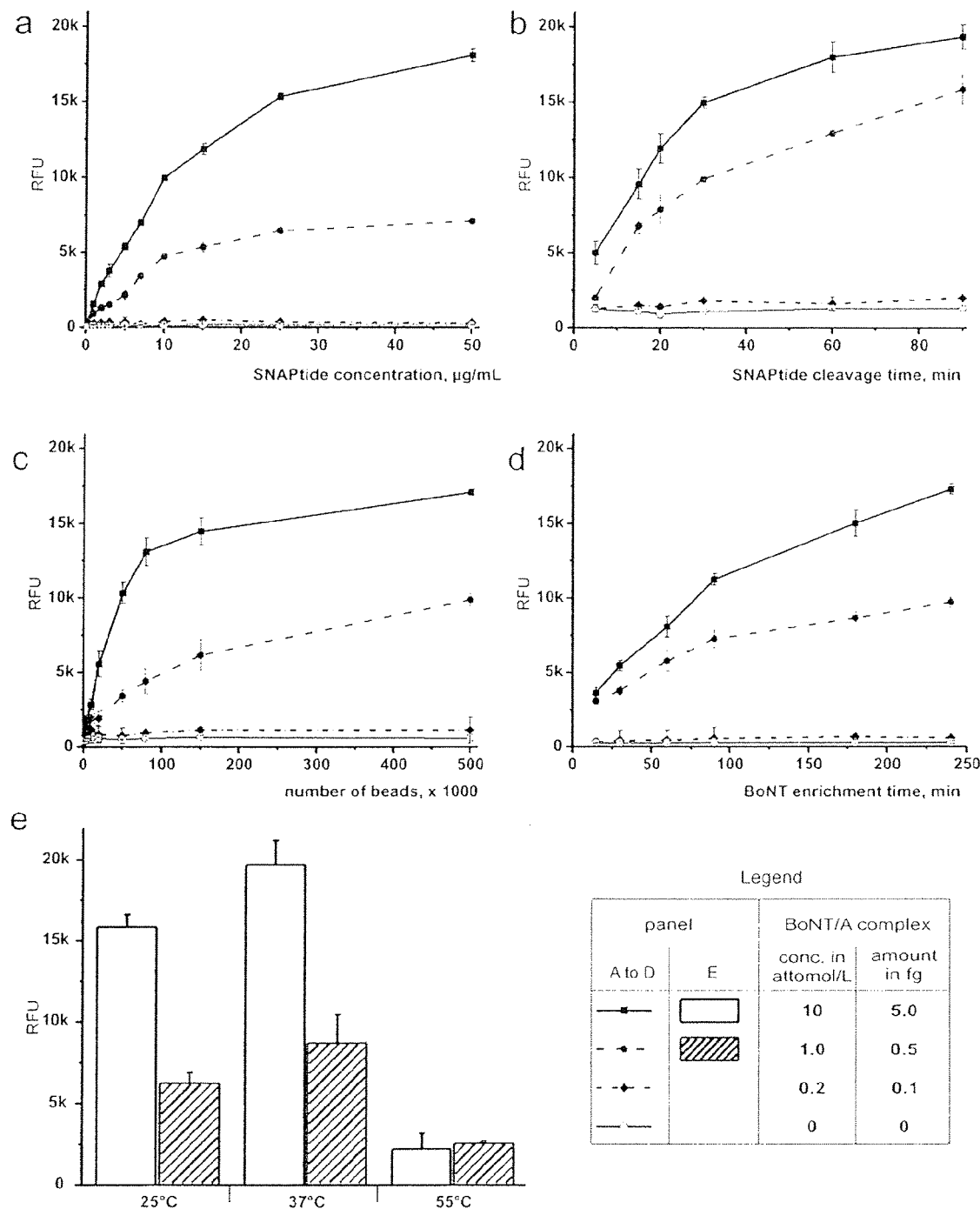
FIG. 3 shows an optimization of assay parameters. (A) BoNT/A concentration-dependent cleavage of SNAPtide after one hour reaction time in 1 ml 10% FBS. (B) SNAPtide (25 µg/ml) conversion time-curve by BoNT/A. (C) Effect of the number of beads exposed for 3 hours to 1 ml 10% FBS spiked with BoNT/A. (D) Time course of BoNT/A enrichment on the beads. (E) Effect of temperature on binding of bead-immobilized BoNT/A (from complex) at one hour incubation time.

BoNT/A was captured and enriched on a bead-based immuno-affinity matrix and cleansed from unspecific binding molecules. The enrichment matrix consisted of protein-A conjugated sepharose beads coupled and cross-linked to polyclonal anti-BoNT/A antibodies (FIG. 1*a*). Anti-BoNT/A antibodies were bound and then covalently cross-linked to the bead-immobilized protein A molecules to prevent bleeding off when mixed with sample. The release of antibodies into the sample may otherwise lower the sensitivity of the assay. Capture antibodies were directly and covalently linked to the Protein A support (agarose beads) using the SeizeX Immunoprecipitation Kit (Pierce) as described in the supplier's protocol. Briefly, 125 μg of *Clostridium botulinum* A Toxoid, formaldehyde inactivated Type A neurotoxin (ab 20641) prepared in 0.4 mL of Binding/Wash buffer contained 0.14 M NaCl, 0.008 M sodium phosphate, 0.002 M potassium phosphate and 0.01 M KCl, pH 7.4, were bound and immobilized to a Protein A support using cross-linker Disuccinimidyl suberate (DSS). 25 μL DSS, dissolved in DMSO immediately before use, was added to the spin cup containing the bound antibody support and gently mixed for 30-60 minutes, centrifuged and washed 4 times with 500 μL of Immunopure Gentle Elution Buffer (Product No. 21027) with a high-salt, neutral pH elution system to quench the reaction and to remove excess DSS and uncoupled antibody. Alternatively, the beads were centrifuged and washed three times with 500 ul Gentle Elution Buffer and two times with 500 ul Gentle Binding Buffer (Pierce Product No. 21030). The Handee™ Spin Cup Columns with functionalized beads were wrapped with laboratory film to prevent gel from drying and stored at 4° C. until used in experiments. The number of beads varying in sizes between 10-100 μm was estimated microscopically with Reichert Bright-Line Metallized Hemacytometer (Hausser Scientific, USA). The immobilized polyclonal rabbit antibody used herein exhibited binding affinity to the light and heavy chain of BoNT/A, as confirmed by Western blot (FIG. 2*b*).

BoNT/A assay with a large immuno-sorbent surface area (ALISSA). The enzymatic activity of the immobilized BoNT/A was determined by cleavage of the specific fluorigenic substrate SNAPtide, a synthetic, commercially available, 13-amino acid peptide that contains the native SNAP-25 cleavage site for BoNT/A (Schmidt 2003; U.S. Pat. No. 6,504,006) (FIG. 1*b*). BoNT/A holotoxin or its complex, were pre-incubated (where indicated) in 5 mM dithiothreitol (DTT) for 30 minutes at 37° C. in order to reduce and pre-activate the enzyme, immediately following reconstitution in the buffer containing 20 mM HEPES, pH 8.0, 0.05% Tween-20, 0.3 mM $ZnCl_2$, and 1.0 mg/mL BSA to recover of BoNT/A. Pre-activated toxin was used immediately after reconstitution with the buffer. Enzyme was immobilized on the antibodies-bound beads in 1 mL of 3% Carnation non-fat milk in PBS or in a 10% Fetal Bovine Serum (heat inactivated). After the addition of immunomatrix samples were incubated with the food matrix or serum. Suspensions were rotated for indicated times at 8 rpm on a Labquake Shaker/Rotisserie (BarnsteadInternational, Dubuque, Iowa). The antibody-bound beads with immobilized enzymes were separated by the centrifugation, washed three times with 500 μl PBS buffer, collected and re-suspended in 300 μl of 20 mM HEPES buffer, containing 0.3 mM $ZnCl_2$, 1.25 mM DTT and 0.1% TWEEN-20, pH 8.0. Unbound material was then removed by washing and synthetic peptide was added. Reaction was started by rotating and adding various concentrations of SNAPtide. For assays 4 mM DMSO-stock solution was diluted in 20 mM HEPES, pH 8.0, and a 100 μM stock solution was used. Assays were performed for indicated times in a dark; reaction was stopped by transfer to ice and addition of a 20 mM ethylenediaminetetraacetate (EDTA) (pH 8.0), which was equally effective in blocking the proteolytic activity of both holotoxin and complexed BoNT/A. For work without antibodies-bound beads, the toxin was combined with the same number of beads with no antibodies or with the rabbit IgG-beads.

Conversion of SNAPtide releases the N-terminal fluorophore, fluorescein-thiocarbomoyl (FITC), which is initially quenched by the C-terminal chromophore, 4-((4-(dimethylamino)phenyl)azo)benzoic acid, succinimidyl ester DABCYL, was recorded with Wallac 1420 Multilabel Counter Victor$^{2}$™ spectrophotometer (PerkinElmer) or with SpectraMax M2 (Molecular Device Corp.) at 485 nm/535 nm as an excitation and emission wavelengths, respectively. The increase in fluorescence intensity is directly proportional to the amount of cleavage that has occurred and thus allows for accurate measurement of botulinum toxin enzymatic activity. Before experiments the beads with cleaved SNAPTide were observed on the glass slides mounted on fluorescent microscope (Olympus BH2-RFCA, Japan). The immobilized polyclonal rabbit antibody used herein did not significantly inhibit the specific proteolytic activity of BoNT/A (FIG. 2*a*).

Example 3

Assay Optimization

The conditions of bead-based assay were optimized to maximize its sensitivity and specificity for one- and ten-attomolar toxin concentrations in 1-mL sample volumes (FIG. 3). Therefore, assay sensitivity was repeatedly measured using serial dilutions of BoNT/A in 10% fetal bovine serum (FBS), and the following parameters were evaluated: antibody-protein A cross-linking conditions, post cross-linking bead wash buffers, number of beads, toxin-antibody binding times and temperature, wash buffers for the removal of non-specific antibody binders, SNAPtide concentration, SNAPtide conversion time and the effect of temperature during reaction. For each BoNT/A dilution, the fluorescence intensity was plotted against the variant parameter (FIG. 3). Due to the asymptotic nature of the resulting curves, there are no optima for several parameters. However, by analyzing the change in signal gain as a function of a given parameter, efficient values for each parameter which produce the steepest increase in signal gain have readily been achieved, and the assay's performance has become robust and predictable.

During synthesis of the bead-based immunomatrix, use of a neutral wash buffer after binding and cross-linking of the antibody to the protein A beads was found to be critical. When an alternative acidic wash buffer (pH 2.8) was used instead, the antibodies were altered such that they became inactive when exposed to nanomolar concentrations of the toxin, probably through toxin-induced proteolytic cleavage.

The assay performed efficiently and with high sensitivity when using about 100 μL/well SNAPtide in concentrations of about 25 μg/mL (FIG. 3*a*) and 1 uM. A reaction time of one hour for the conversion of the fluorigenic SNAPtide at room temperature (25° C.) was appropriate (FIG. 3*b*). Within limits, the signal-gain of the assay can be enhanced by increasing the number of beads mixed with the sample (FIG. 3c) and by extending the enzyme enrichment time as demonstrated in FIG. 3d. The most efficient bead concentrations lie between about 100,000 and about 120,000 beads/mL, which correspond to a bead bed volume of approximately 8.7-10.4 µl or approximately 10-12 µl, when left to settle. Further increase of the bead concentration to 500,000/mL raised the signal intensity only by another 28% (FIG. 3c). The effect of temperature on the toxin capturing step was also investigated. Sufficient binding required about 3 hrs at about 25° C. incubation for the substrate with the beads, and about one hour when at about 37° C. The measured toxin activity was significantly diminished at about 55° C. (FIG. 3e), likely due to toxin deactivation rather then due to decreased antibody binding. An increase in temperature from about 25° C. to about 37° C. during the SNAPtide-conversion reaction improved the signal and reliable readings were obtained for reaction times of about 1 hour.

Pre-activation of the toxin on the beads during the wash step was achieved with 5 mM DTT and produced slightly higher signals when compared to the non-pre-activated toxin (FIG. 4a). However, the subsequent reaction with the fluorigenic reporter had to be performed in 1.25 mM DTT in order to avoid denaturation of the immunoaffinity matrix and because prolonged exposure to the more concentrated reductive agent inactivated the toxin considerably (tested on bead-free toxin).

Example 4

Assay Performance

Sensitivity

Figure 5:
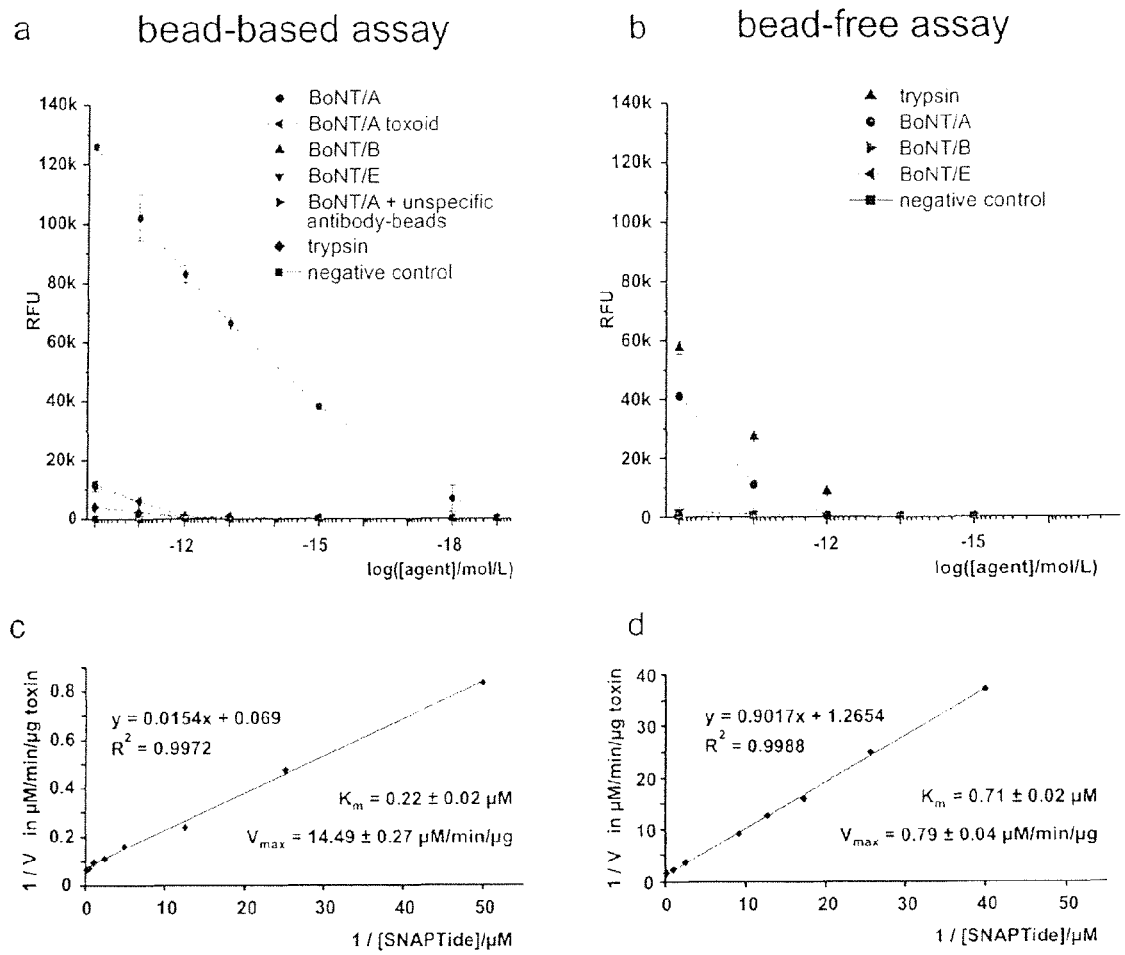
FIG. 5 shows a comparison of the specificity, sensitivity and kinetics of bead-based ALISSA (FIG. 5A) and bead-free assays (FIG. 5B).

The 150-kDa BoNT/A holotoxin (from two different commercial sources) and the 500-kDa BoNT/A complex were serially diluted and tested by BoNT/A ALISSA in 10% fetal bovine serum (FBS) (FIG. 4A). Significant signals of several thousand relative fluorescence units (RFU) were still observed for concentrations of one attomol/L in 1-mL sample volumes. Signals for toxin complex were always stronger then for identical molar concentrations of holotoxin. The practical detection limit in the diluted serum was extrapolated to be ~0.5 attomol/L, which corresponds to 250 attogram toxin complex in 1 mL sample (FIGS. 3, 4a). To determine ALISSA use in complex samples, the assay's sensitivity for the toxin complex was also determined in spiked undiluted human serum, carrot juice, reconstituted non-fat powdered milk, fresh milk, and gelatin phosphate (GP) diluent (FIG. 4B). GP diluent is typically used in the life mouse toxicity bioassay. Although somewhat lower than in toxin-spiked samples with 10% FBS, discernable fluorescent intensities above background were still detected for 1 attomol/L toxin complex, with signal intensities of ~14,800, ~14,750, ~3100, ~2500 and ~650 RFU above background in undiluted human serum, 50% carrot juice, GP diluent, non-fat milk and fresh milk, respectively. A fat-solubilizing wash buffer (with HEPES) was required for analyses of fresh milk samples. Overall, the ALISSA signals correlate proportionally with the toxin concentration over several orders magnitude (FIG. 4).

The ALISSA performed with comparable sensitivities in undiluted human serum, 50% carrot juice (adjusted to pH 7.5 with binding buffer), reconstituted powdered milk, fresh milk and GP-diluent. In direct comparison with the mouse assay, the ALISSA was considerably faster and 4-5 orders of magnitude more sensitive.

Example 5

Assay Performance

Specificity and Kinetics

Specificity of the assay and sensitivity and kinetics of the bead-based ALISSA compared to those of the bead-free conversion of the reporter peptide were tested. To test non-specific agents, serum samples were utilized with: 1) beads conjugated to purified nonspecific rabbit IgG; 2) trypsin, because it is also able to cleave SNAPtide, but cannot be enriched on the beads; 3) BoNT type B complex; 4) BoNT type E complex; 5) type A toxoid, which is a non-toxic, antibody-binding formaldehyde inactivated derivative of BoNT/A; and 6) a toxin-free control (FIG. 5a, 5b). The bead-based assay produced low intensity signals with the non-specific agents trypsin, BoNT/A toxoid, BoNT/B and E) and only at the highest tested concentrations of 10-100 pmol/L. The bead-free reaction mixture yielded signals only with trypsin and BoNT/A for concentrations of 1 pmol/L or greater, and these signals were weak. Equimolar trypsin concentrations led to even higher signals than the BoNT/A complex. Toxin type B and E complexes, for which the peptide substrate does not contain specific cleavage sites, produced very weak signals only at the 10 and 100-picomolar concentrations that were even lower than those obtained with the bead-based assay. Interestingly, the bead-based detection of BoNT/A produced significantly higher signals—at any given toxin dilution step—than did the bead-free reaction mixture. For the bead-free reaction mixture discernable signals were only obtained for BoNT/A concentrations greater or equal to 1 pmol/L. In contrast, strong signals were obtained with BoNT/A at concentrations as low as 1 attomol/L when used in the bead-based assay. For the comparison of bead-free versus bead-based assay, toxin concentrations and total toxin amounts were identical in each dilution step.

This remarkable enhancement of the substrate cleavage reaction as a response to BoNT/A immobilization prompted a determination of the kinetic parameters of the SNAPtide conversion reaction. For comparative purposes, fixed total BoNT/A complex concentrations of 100 pmol/L were used in 1-mL sample volumes for both the reactions with the free and with the bead-immobilized toxin. At this concentration, BoNT/A is safely detected with either method. Kinetic constants were obtained from plots of initial rates versus eight concentrations of substrate ranging 0.0125 to 5 μM. (Blanch and Clark, 1997; Liu et al., 1999). Initial velocity for reactions were calculated from linear regression analysis as μM of cleaved SNAPTide/min/mg enzyme. The values are the averages of 4 independent determinations±error propagation. The Km value for the BoNT/A was calculated from the Lineweaver—Burk double reciprocal plot. No-enzyme reference was applied in establishing baseline RFU when there is no enzyme activity. This control contained all components of the BoNT/A reaction mixture except the enzyme, replaced with the equivalent volume of reaction buffer. Background fluorescence was determined by using wells with only SNAPtide. Results are the averages of triplicate determinations The hydrolysis of SNAPtide by BoNT/A obeys Michaelis-Menten kinetics and is characterized by a linear relationship between the reciprocal substrate concentration and the activity of the enzyme (FIGS. 5c, 5d). Michaelis constancies ($K_m$) and maximal conversion rates ($V_{max}$) were calculated from the linear regression of the reciprocal SNAPtide concentration 1/[SNAPtide] versus the reciprocal reaction rate (1/V). The $K_m$ of the immobilized enzyme is 3.2-fold lower than for the free enzyme, suggesting a slightly higher enzyme/substrate affinity. Interestingly, the main effect was found in the rate of catalysis: the immobilized BoNT/A is capable of converting its substrate with an 18-fold increased maximal conversion rate than the free toxin. The corresponding values for $V_{max}$ at 25° C. were 0.79±0.04 µM/min/µg and 14.49±0.27 µM/min/µg for free (non-immobilized) and immobilized enzymes, respectively.

Example 6

Assay Performance

Comparison of BoNT/A ALISSA with the Live Mouse Assay.

A split aliquot of 100 ng BoNT/A toxin complex was shipped in a refrigerated hazmat container to collaborators at the Infant Botulism Treatment and Prevention Program of the California Department of Public Health (CDPH) in Richmond for use in the diagnostic life mouse bioassay. Identical dilution series of the toxin in GP-diluent were prepared concurrently in pre-prepared and weighed vials at both institutions. The approximate time of the i.p. mouse injections at the two locations coincided by a margin of minutes. Mice weighing 18-22 g each were injected i.p. with 0.5 mL/mouse of sample and watched for signs of botulism or death for the standard 96 hour observation period. The results of BoNT/A ALISSA became available after ~2.5 hours and mice were observed for three days (Table 2).

The mouse assay was positive for the highest test concentrations of 300 and 60 pg/mL (0.5 mL injected per mouse). Mild symptoms of botulism developed within 96 hours in three of five mice that received one hundreds of the theoretical $LD_{50}$ (0.3 pg). All other animals that received $10^{-4}$ or $10^{-5}$ $LD_{50}$ remained completely disease free and asymptomatic. BoNT/A ALLISA produced clear signals throughout the dilution series. The lowest BoNT/ALLISA fluorescence signal at the lowest test concentration was 0.6 fg/mL ($10^{-5}$ $LD_{50}$), which is still ~3,100 units above background levels.

TABLE 2

Comparison of the mouse bioassay with BoNT/A ALISSA

| [complex] (fg/mL) | $LD_{50}s^a$ | Mouse bioassay result | ALISSA result (RFU) |
|---|---|---|---|
| 300,000.0 | 5 | 5/5 dead in <4 hrs | 51,105 ± 95 |
| 60,000.0 | 1 | 5/5 dead in <21 hrs | 48,009 ± 464 |
| 600.0 | $10^{-2}$ | 3/5 mild symptoms[b] | 28,049 ± 1713 |
| 6.0 | $10^{-4}$ | 5/5 disease free[b] | 13,954 ± 1324 |
| 0.6 | $10^{-5}$ | 5/5 disease free[b] | 3,116 ± 15 |
| 0.0 | 0 | n.d. | 0 ± 8 |

[a]calculated per injected 0.5 ml sample; one $LD_{50}$ = 30 pg BoNT/A complex;
[b]all mice alive after 69 hrs;
n.d., not determined The BoNT/A ALISSA avoids interference with other sample components by using a highly BoNT/A-specific affinity matrix and by using a BoNT/A-specific substrate to exploit the natural proteolytic activity of the toxin. Both steps also amplify the signal by 1) localized enrichment of the toxin; and 2) through enzymatic conversion of billions of substrate molecules per toxin molecule. The capture matrix is designed to stably enrich the toxin, while retaining its enzymatic activity and by purifying the toxin from other non-specific proteases contained in the sample. The beaded-protein A matrix binds to the antibodies via the Fc regions, orienting the antigen binding domains away from the bead surface and into the surrounding sample fluid. This provides higher accessibility to target toxin molecules.

The plateaus observed in the assay's response curves used to optimize substrate concentration and size and volume proportions of the immunosorbent matrix represent saturation effects that indicate when the substrate concentration is no longer rate-limiting. Antibody binding capacity was about 50 ug antibody per one million beads which estimates to an antibody dissociation constant kD at half maximum saturation to be approximately 15 nM. Use of antibodies having higher binding affinity will increase assay sensitivity. High affinity anti-BoNT antibodies have been used as antitoxins to neutralize systemic botulinum toxin in botulism patients (Marks 2004; Garcia-Rodriguez 2007). This mode of "neutralization" however, should not be confused with inactivation of the toxin's enzymatic activity by steric hindrance of the catalytic site resulting from antibody binding. Antibody-mediated "neutralization" of toxin in vivo depends on formation of antibody-antigen complex and hepatic accumulation and clearance (Ravichandran 2006; Simpson 2001).

Figure 6:
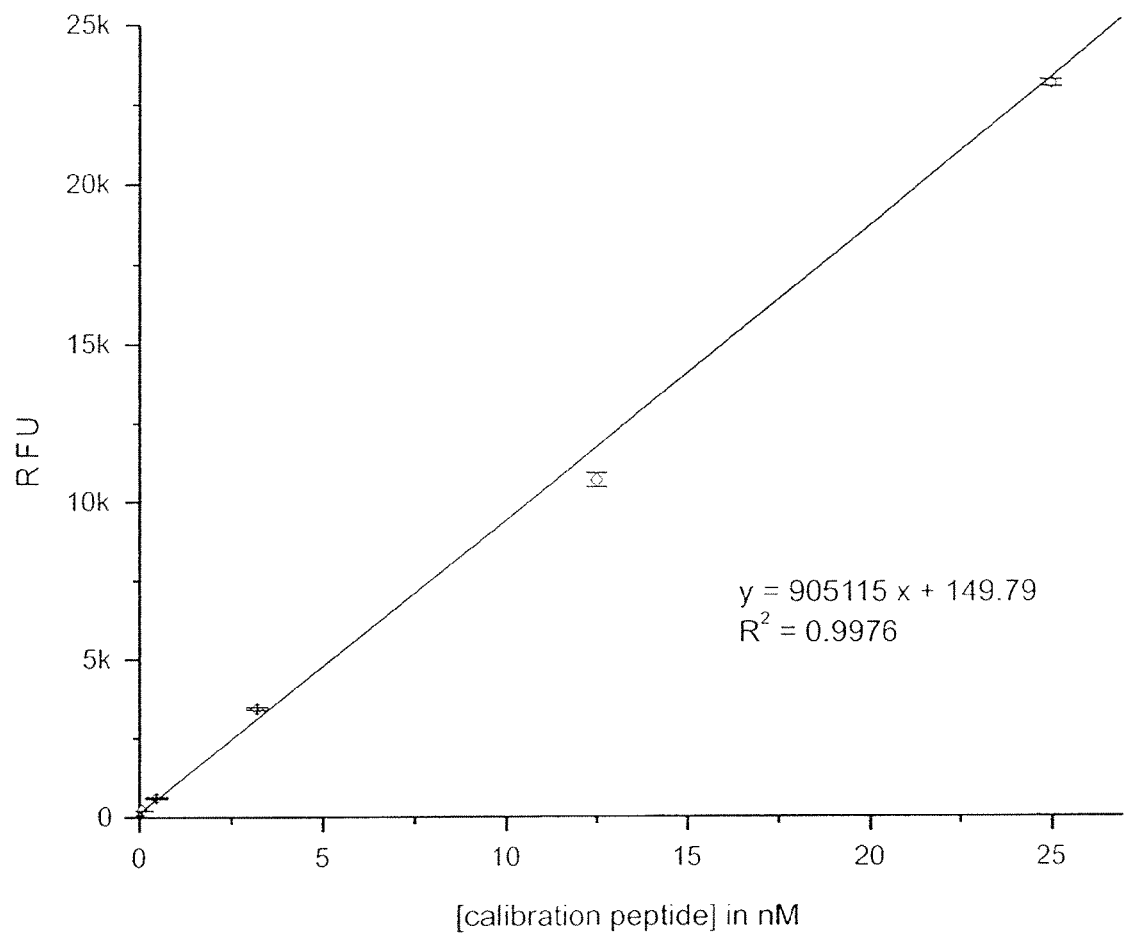
FIG. 6 shows a standard curve of the fluorescence signal of the unquenched calibration peptide, which is structurally identical to the FITC-containing cleavage product resulting from BoNT/A hydrolysis of SNAPtide by BoNT/A; "Y" in RFU; "x" in nM; "R" is the correlation coefficient.

Use of a standard curve to measure concentration-dependent intensity of fluorescence signal of un-quenched calibration peptide (FIG. 6) allowed determination of the molar conversion rate for the substrate molecules. A calculated substrate conversion rate of approximately two billion substrate molecules per one immobilized toxin molecule per hour was calculated for the 10 attomolar toxin concentration. The reaction being limited by the rate at which the toxin becomes inactivated. Factors such as chelation of the zinc atom by DTT, denaturation of the toxin by the reducing buffer, or proteolytic degradation of the toxin either through autoproteolysis or by a contaminant protease may also contribute to inactivation of the toxin.

In certain embodiments, optimal temperature is 37° C. coincident with the temperature at which the natural action of the toxin occurs and at which IgG antibody binding may be optimal. Higher temperatures may inactivate the toxin. Preferably, the pH of the sample is approximately neutral (between about 6 and about 8). Assay sensitivity may also be further increased by reducing background fluorescence of uncleaved substrate such as uncleaved SNAPtide.

In certain embodiments, a peptide conjugated FRET pair with a 2,4-dinitrophenyl acceptor and a 4-methyl-7-dimethylamino-coumarin donor may be used as a substrate. These and other FRET pairs having better spectral overlap can allow lower background fluorescence with good kinetic properties.

In certain embodiments, an approximately 18-fold increase in maximum conversion rate $v_{max}$ and a three-fold higher affinity to the substrate (three-fold lower $k_M$) for the immobilized toxin was observed as compared to free toxin in solution (FIGS. 5C and 5D). The average bead surface area in the ALISSA assay is approximately 7.85 $cm^2$ per sample (based on a 50 µm average bead diameter) whereas the antigen-binding surface area in a conventional solid-phase or solid-state ELISA with a 96-well flat-bottom microplate measures only about 0.256 $cm^2$ per well. Thus, the available reaction surface area in the ALISSA is about 30-fold greater than provided by prior art methods. Such immobilized toxin is also better protected from proteolysis and aggregation. Molecules of unstable BoNT/A light chain are sufficiently separated to diminish any autocatalytic degradation. Use of bead-based assay also allows for more stringent wash procedures thereby diminishing interference by other proteases. This was demonstrated for BoNT/A when compared to equimolar concentrations of trypsin, BoNT/B and BoNT/E. The increased reaction surface area and control of diffusion through more frequent substrate-enzyme interactions also contributes to the improved enzymatic activity.

Example 7

Fluorogenic Substrates

Figure 8:
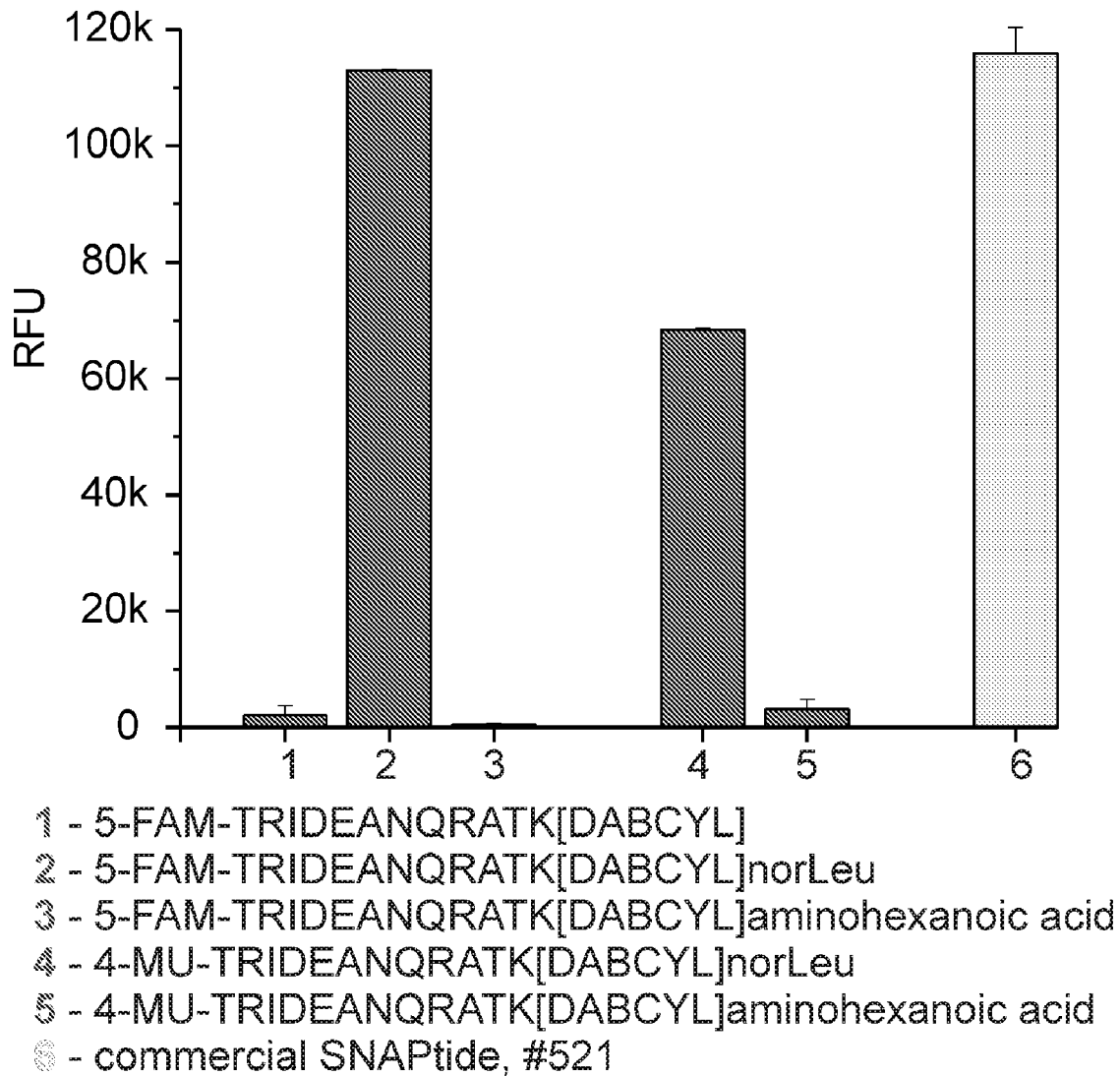
FIG. 8 shows analysis of alternative fluorogenic BoNT/A substrates as compared with commercial SNAPtide. About 5 µM substrate solutions were incubated with 2 nM BoNT/A complex for 1 hr at 37° C. 1 to 5 indicate COH-made synthetic BoNT/A and their sequences (1-SEQ ID NO:20; 2-SEQ ID NO: 21; 3-SEQ ID NO:19; 4-SEQ ID NO:22; 5-SEQ ID NO:5); 6 commercial SNAPtide; DABCYL is 4-(dimethylaminoazo) benzene-4-carboxylic acid conjugated to the c-amino group of lysine.
Figure 9:
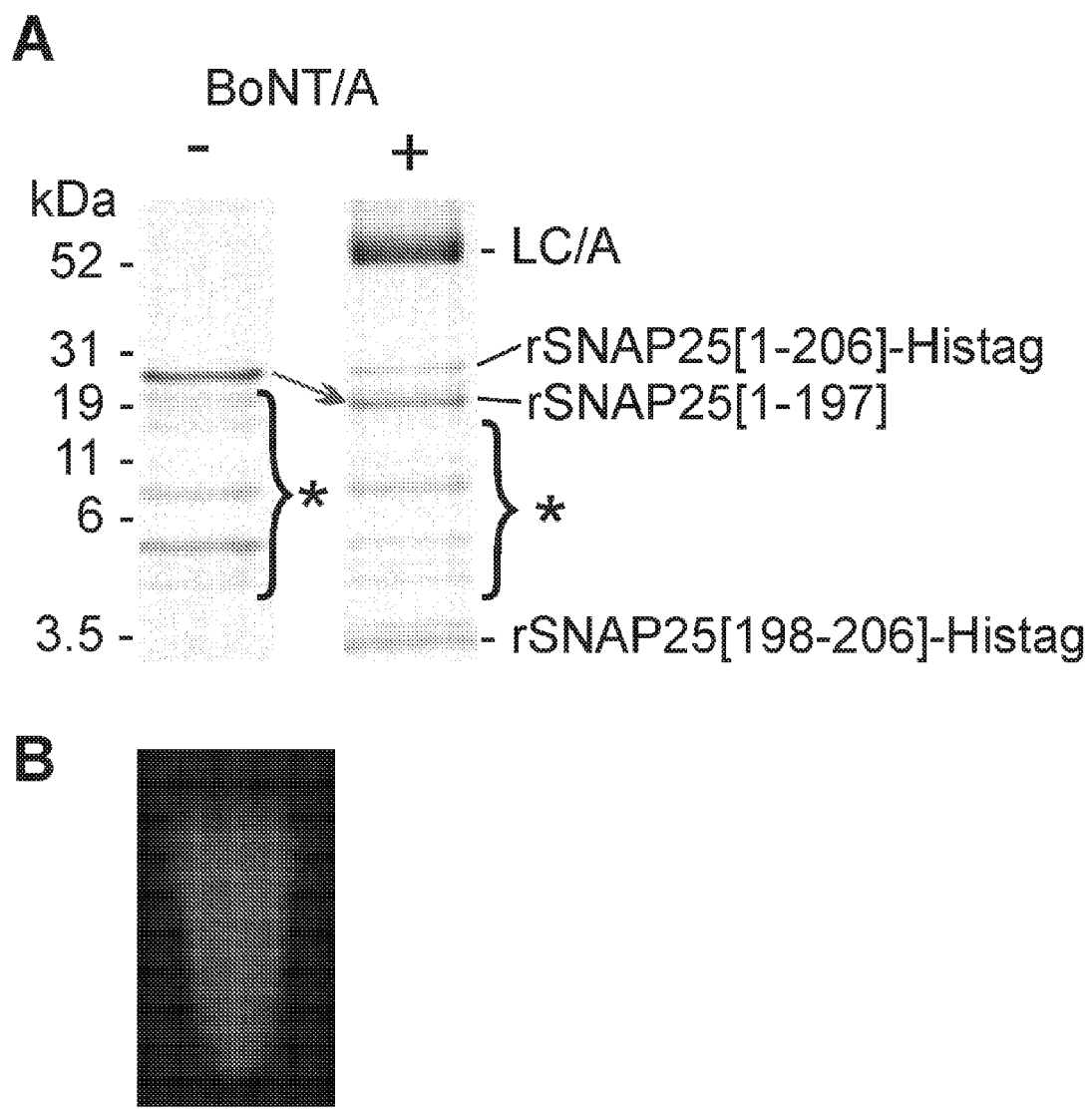
FIG. 9 shows (A) SDS-PAGE analysis of recombinant human SNAP-25 proteolysis reaction in presence of BoNT/A. The gel shift is indicated by the arrow. *E. coli* protein impurities are denoted by asterisk. The small cleavage product contains the C-terminus of rSNAP25 with the hexahistidine tag and measure about 4 kDa in size. (B) photograph of an eppendorf tube with light-emitting *E. coli* expressing his-tagged FFL.

Fluorogenic peptides were synthesized using standard Fmoc chemistry methodology well known in the art. Commercial SNAPtide (List Biological Laboratories) contains a fluorescein isothiocyanate (FITC)-labeled N-terminus and a thiourea group that is unstable over time or when in the presence of acids. This can result in undesired background signal. To avoid this, different SNAPtide-like peptides that were N-terminally labelled with either 5-carboxyfluorescein (5-FAM)- or 4-Methylumbelliferone (4-MU) were synthesized. The resulting BoNT substrates contain stable peptide bonds and are readily cleaved by BoNT/A (FIG. 8).

The effect of the substrate's C-terminal amino acid corresponding to M202 in the native human SNAP-25 sequence (SEQ ID NO: 11) was also determined. Commercial SNAPtide replaces the M202 in the native sequence with a Norleucine residue. This Norleucine residue provided efficient cleavage of the substrate as deletion or replacement with 6-aminohexanoic acid greatly diminished the efficiency of the BoNT/A-mediated cleavage reaction (FIG. 8). The Norleucine used is a non-oxidizable surrogate for the methionine residue located at 202. Substrates having 6-aminohexanoic acid in place of the Norleucine residue located at 202 as shown in FIG. 8 are:

5-Fam-ThrArgIleAspGluAlaAsnGlnArgAlaThrLys
[DABCYL]Hex (SEQ ID NO: 19); and
4-MU-ThrArgIleAspGluAlaAsnGlnArgAlaThrLys
[DABCYL]-Hex (SEQ ID NO: 5);

wherein Hex is 6-aminohexanoic acid.

By applying a molecular modelling and docking approach, several novel substrates were produced (Tables 3-5; SEQ ID NOS: 12-14). The chemical structures (identified as "1", "2" and "3") of each exemplary substrate is depicted below its corresponding table listing of amino acid sequence. In the below exemplary embodiments, each of the novel peptide substrates contained 12 amino acid residues. In addition, control peptides having and RA to EL mutation (indicated in bold text) were produced (Table 6; SEQ ID NOS: 15, 17-18). The BoNT/A protease cannot efficiently cleave these peptides while other proteases are able to cleave these peptides, making them suitable control peptides for use in the ALISSA. The control peptides (Table 6; SEQ ID NOS: 15, 17-18) allows compensation for the background signal resulting from non-BoNT/A protease activity or non-target protease activity.

TABLE 3

| K[5-Fam]IDEANQRATK[DABCYL]X-amide (SEQ ID NO:12) | | |
|---|---|---|
| Number | 1-letter code | Amino acid name and modification |
| 1 | K[5-Fam] | Lysine with 5-carboxyfluorescein conjugated to its ε-amino group |
| 2 | I | Isoleucine |
| 3 | D | Aspartic acid |
| 4 | E | Glutamic acid |
| 5 | A | Alanine |
| 6 | N | Asparagine |
| 7 | Q | Glutamine |
| 8 | R | Arginine |
| 9 | A | Alanine |
| 10 | T | Threonine |
| 11 | K[DABCYL] | Lysine with DABCYL conjugated to its ε-amino group |
| 12 | X | Norleucine with an amide C-terminus |

TABLE 3-continued

K[5-Fam]IDEANQRATK[DABCYL]X-amide (SEQ ID NO:12)

| Number | 1-letter code | Amino acid name and modification |
|---|---|---|

1)

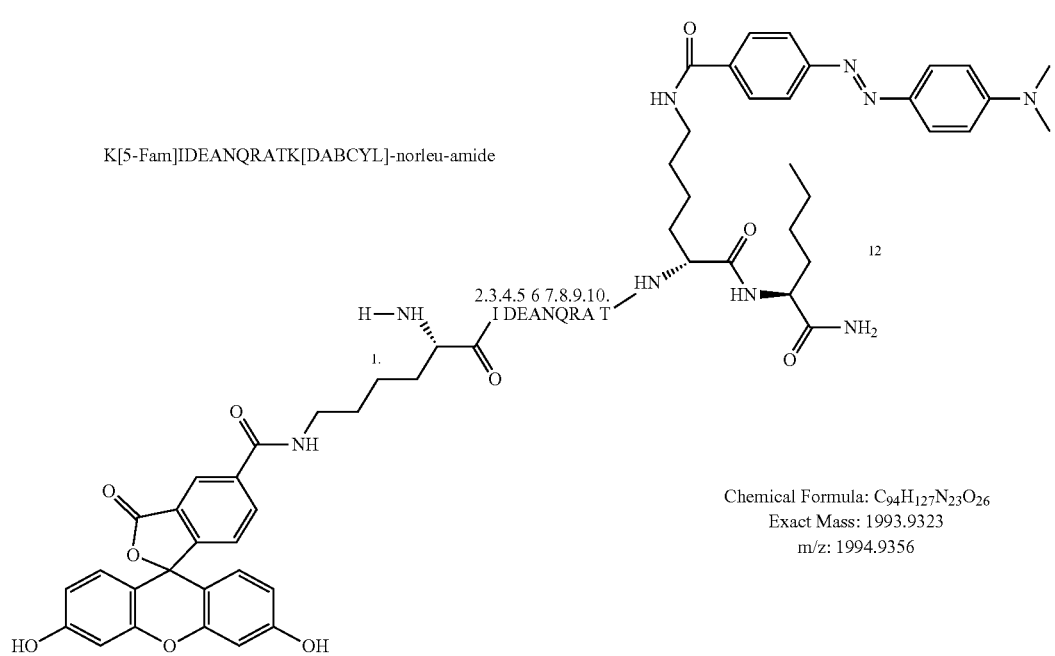

K[5-Fam]IDEANQRATK[DABCYL]-norleu-amide

Chemical Formula: $C_{94}H_{127}N_{23}O_{26}$
Exact Mass: 1993.9323
m/z: 1994.9356

TABLE 4

Fam-K[5-Fam]IDEANQRATK[DABCYL]X-amide (SEQ ID NO:13)

| Number | Code | Amino acid name and modification |
|---|---|---|
| 1 | 5-Fam-K[5-Fam] | Lysine with a 5-carboxyfluorescein conjugated to its α and ε-amino groups |
| 2 | I | Isoleucine |
| 3 | D | Aspartic acid |
| 4 | E | Glutamic acid |
| 5 | A | Alanine |
| 6 | N | Asparagine |
| 7 | Q | Glutamine |
| 8 | R | Arginine |
| 9 | A | Alanine |
| 10 | T | Threonine |
| 11 | K[DABCYL] | Lysine with DABCYL conjugated to its ε-amino group |
| 12 | X | Norleucine with an amide C-terminus |

TABLE 4-continued

Fam-K[5-Fam]IDEANQRATK[DABCYL]X-amide (SEQ ID NO:13)

| Number | Code | Amino acid name and modification |
|---|---|---|
| 2) | | |

5-Fam-K[5-Fam]IDEANQRATK[DABCYL]-norleu-amide

Chemical Formula: $C_{115}H_{137}N_{23}O_{32}$
Exact Mass: 2351.9800
m/z: 2352.9834

TABLE 5

Alternative to above 2 substrates:
5-Fam-KIDEANQRATK[DABCYL]X-amide (SEQ ID NO: 14)

| Number | Code | Amino acid name and modification |
|---|---|---|
| 1 | 5-Fam-K | Lysine with a 5-carboxyfluorescein conjugated to its α-amino group |
| 2 | I | Isoleucine |
| 3 | D | Aspartic acid |
| 4 | E | Glutamic acid |
| 5 | A | Alanine |
| 6 | N | Asparagine |
| 7 | Q | Glutamine |
| 8 | R | Arginine |
| 9 | A | Alanine |
| 10 | T | Threonine |
| 11 | K[DABCYL] | Lysine with DABCYL conjugated to its ε-amino group |
| 12 | X | Norleucine with an amide C-terminus |

TABLE 6

5-Fam-K[(5-Fam]IDEANQELTK[DABCYL]X-amide (SEQ ID NO: 15);
5-Fam-KIDEANQELTK[DABCYL]X-amide (SEQ ID NO: 17); and
K[5-Fam]IDEANQELTK[DABCYL]X-amide (SEQ ID NO: 18).

| Number | Code | Amino acid name and modification |
|---|---|---|
| 1 | 5-Fam-K[5-Fam]; 5-Fam-K; or K[5-Fam] | Lysine with a 5-carboxyfluorescein conjugated to either its α or ε-amino group or to both (there are three possibilities) as illustrated by SEQ ID NOS: 15, 17 and 18) |
| 2 | I | Isoleucine |
| 3 | D | Aspartic acid |
| 4 | E | Glutamic acid |
| 5 | A | Alanine |
| 6 | N | Asparagine |
| 7 | Q | Glutamine |
| 8 | E | Glutamic acid |
| 9 | L | Leucine |
| 10 | T | Threonine |
| 11 | K[DABCYL] | Lysine with DABCYL conjugated to its ε-amino group |
| 12 | X | Norleucine with an amide C-terminus |

These exemplary control peptides cannot be efficiently cleaved by botulinum neurotoxin serotype A, but can be cleaved by other proteases. Hence they can be used in the ALISSA assay as a control for non-specific (non-BoNT/A) protease activity. Below is the structure of one (SEQ ID NO: 18) of the three possible versions of the control peptide.

3) Control Peptide

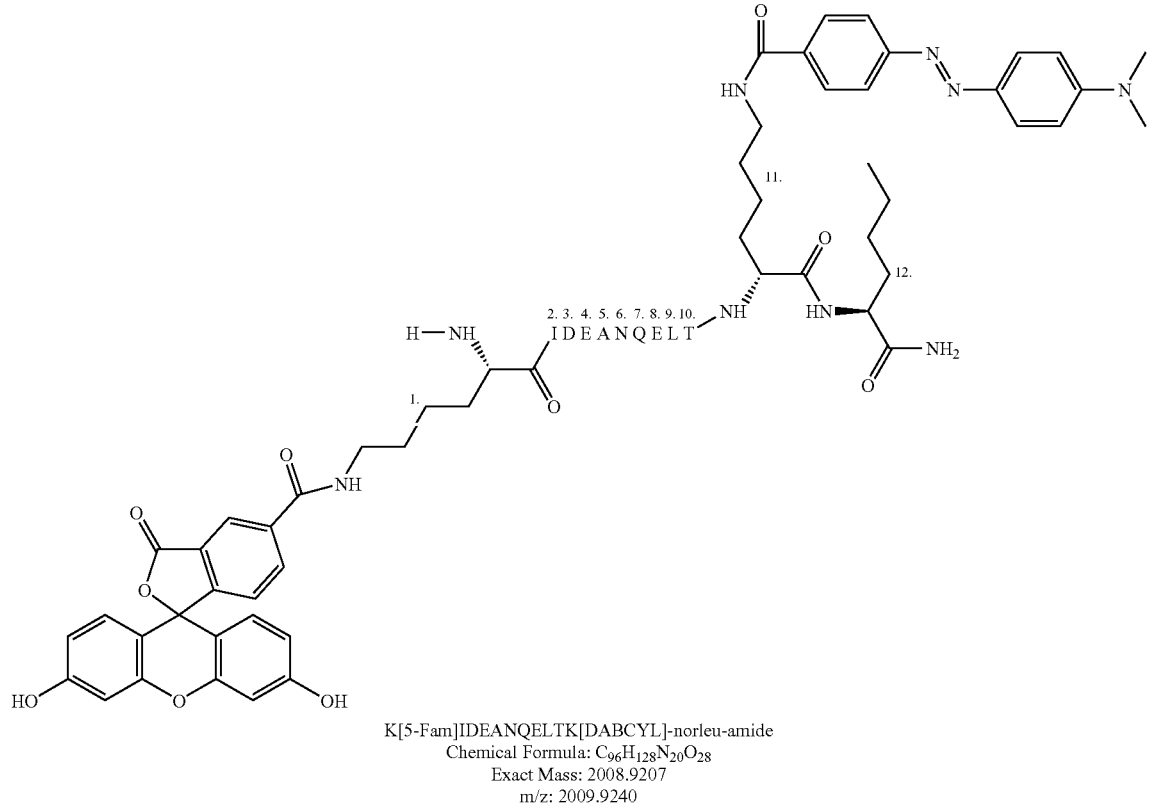

K[5-Fam]IDEANQELTK[DABCYL]-norleu-amide
Chemical Formula: C₉₆H₁₂₈N₂₀O₂₈
Exact Mass: 2008.9207
m/z: 2009.9240

By employing the above-described methods, several new substrates were identified for use in the ALISSA assay. The substrates contain 12 amino acid residues and exhibited higher chemical stability and high sensitivity for BoNT detection when used as substrate. These substrates include, but are not limited to:

Lys[5-Fam]IleAspGluAlaAsnGlnArgAlaThrLys[DABCYL]X (SEQ ID NO:12), wherein X is Nle or 6-aminohexanoic acid, 5-Fam-Lys[5-Fam]IleAspGluAlaAsnGlnArgAlaThrLys[DABCYL]Nle (SEQ ID NO:13)

5-Fam-LysIleAspGluAlaAsnGlnArgAlaThrLys[DABCYL]Nle (SEQ ID NO:14); and

LysIleAspGluAlaAsnGlnArgAlaThrLysNle (SEQ ID NO: 16). Peptides useful as control substrates were also generated by employing the above-described methods.

Said control substrates include, but are not limited to:

(4-MU)-ThrArgIleAspGluAlaAsnGlnArgAlaThrLys[DABCYL]Hex (SEQ ID NO: 5)

5-Fam-Lys[5-Fam]IleAspGluAlaAsnGlnGluLeuThrLys[DABCYL]Nle (SEQ ID NO:15)

5-Fam-LysIleAspGluAlaAsnGlnGluLeuThrLys[DABCYL]Nle (SEQ ID NO: 17)

Lys[5-Fam]IleAspGluAlaAsnGlnGluLeuThrLys[DABCYL]Nle (SEQ ID NO: 18)

(5-Fam)-ThrArgIleAspGluAlaAsnGlnArgAlaThrLys[DABCYL]Hex (SEQ ID NO: 19)

wherein Hex is 6-aminohexanoic acid.

Example 8

Bioluminescent Substrates

A series of protein engineering experiments were conducted to determine whether extended sequences of recombinant SNAP25 can be expressed in bacteria and remain cleavable by BoNT. Experiments were also conducted to determine whether recombinant firefly luciferase (FFL) with C-terminal histidine tags or other modifications remain functional. Functional recombinant SNAP25 (rSNAP25) was expressed using commercial brain cDNA library. Gel-shift experiment demonstrated that rSNAP25 is readily cleaved by BoNT/A (FIG. 9) while having a C-terminal hexahistidine tag. The rSNAP25 was also cleaved at a faster rate as compared to fluorogenic peptide SNAPtide. To generate recombinant FFL, a firefly luciferase yeast plasmid (pGAL-FFL) was obtained from a gene depository and used as a template to construct a pET-vector based on recombinant firefly luciferase expression system. The recombinant FFL had a C-terminal hexahistidine tag and was readily expressed in *E. coli*. When FFL-expressing bacteria were combined with 5-fluoroluciferin, the resulting light signal was strong enough to be visible with the naked eye indicating that the protein was functional (FIG. 9). The signal exceeded the maximally permissible luminescence signal strength of a Victor luminometer plate reader.

Fluorogenic peptide library for producing substrates was established using previously described methods (Aina 2007; Juskowiak 2004; Rosse 2000). Synthetic peptide libraries are generated using natural and non-natural or non-proteinogenic amino acids to improve resistance toward non-target proteases. As described further below, a beaded synthesis resin support was used to perform a one-bead-one-compound approach in which each bead contains only one type of peptide in picomolar quantities. The method used was as described previously (Aina 2005; Lam 2003). On-bead conversion of the substrate was performed for several cycles of selection by first incubating the peptide bead library without BoNT in presence of a relevant sample type (e.g. serum or homogenized mouse organs) for extended periods of time. Peptides containing unstable peptides become fluorescent and were removed by particle sorting using a flow cytometer. The beads that remained non-fluorescent were then exposed to BoNT. Beads that became rapidly fluorescent in presence of BoNT were separated with either a micromanipulator (tetrad dissection microscope at COH) or flow cytometer. The library was constructed such that the peptides can be dissociated from the beads readily (e.g. by CNBr cleavage) in order to allow decoding of the sequence of the fluorogenic substrate by mass spectrometry.

Example 9

One-Bead-One-Peptide Libraries

One-bead-one-peptide libraries were generated by Fmoc (fluoren-9-ylmethoxycarbonyl) chemistry. Using a split and mix approach, the synthetic peptides begin with a block of 3 D-amino acids followed by 5 randomized L-amino acids and another block of 3-D-amino acids. Addition of 3 D-amino acids to the N- and C-termini of a peptide increases its stability. Natural proteinogenic, D-amino acids, rare as well as unnatural amino acids (Table 7) are used. The number of beads used are about three times greater than the number of possible permutations to obtain statistically relevant and reproducible results. For example, if 13 different amino acids are used for synthesis of randomized 5-mer peptides, 1.6 billion compounds are obtained and therefore 3.6 billion beads are screened. When testing a suitable linker with an existing substrate, where an undesired amount of the cleaved fluorophore containing peptide remains on the resin beads used to generate the library, the linker will be tested with existing substrate and if desired, the order of fluorophore and quencher can be reversed. Decoding of the novel fluorogenic substrate sequence is then performed by mass spectrometry analysis.

Listed below in Table 7 are commercially available (e.g. Sigma Chemicals), non-natural amino acids that are suitable for use in generating one or more library of fluorogenic peptides.

TABLE 7

| Short name | Full name, synonym |
|---|---|
| (S)-Fmoc-4-chloro-β-Homophe-OH | (S)-3-(Fmoc-amino)-4-(4-chlorophenyl)butyric acidFmoc-4-chloro-L-β-Homophe-OH |
| (R)-Fmoc-4-fluoro-β-Homophe-OH | (R)-3-(Fmoc-amino)-4-(4-fluorophenyl)butyric acid, Fmoc-4-fluoro-D-β-Homophe-OH |
| (S)-Fmoc-3-cyano-β-Homophe-OH | (S)-3-(Fmoc-amino)-4-(3-cyanophenyl)butyric acid, Fmoc-3-cyano-L-β-Homophe-OH |
| (S)-Fmoc-3-methyl-β-Homophe-OH | (S)-3-(Fmoc-amino)-4-(3-methylphenyl)butyric acid, Fmoc-3-methyl-L-β-Homophe-OH |
| (S)-Fmoc-3-trifluoromethyl-β-Homophe-OH | (S)-3-(Fmoc-amino)-4-[3-(trifluoromethyl)phenyl]butyric acid, Fmoc-3-(trifluoromethyl)-L-β-Homophe-OH |
| (S)-Fmoc-2-trifluoromethyl-β-Homophe-OH | (S)-3-(Fmoc-amino)-4-[2-(trifluoromethyl)phenyl]butyric acid, Fmoc-2-(trifluoromethyl)-L-(β-Homophe-OH |
| (S)-Fmoc-4,4-diphenyl-β-Homoala-OH | (S)-3-(Fmoc-amino)-4,4-diphenylbutyric acid, Fmoc-4,4-diphenyl-D-β-Homoala-OH |
| (S)-3-(Fmoc-amino)-4-(2-naphthyl)butyric acid | Fmoc-4-(2-naphthyl)-L-β-Homoala-OH, Fmoc-β-2-Homonal-OH |
| (R)-Fmoc-4-(3-pyridyl)-β-Homoala-OH | (R)-3-(Fmoc-amino)-4-(3-pyridyl)butyric acid, Fmoc-4-(3-pyridyl)-D-β-Homoala-OH |
| (S)-3-(Fmoc-amino)-5-phenyl-pentanoic acid | Fmoc-5-phenyl-L-β-norvaline |
| (R)-3-(Fmoc-amino)-5-phenyl-pentanoic acid | Fmoc-5-phenyl-D-β-norvaline |
| (S)-3-(Fmoc-amino)-5-hexenoic acid | Fmoc-4-vinyl-L-β-Homoala-OH |
| (S)-3-(Fmoc-amino)-6-phenyl-5-hexenoic acid | Fmoc-4-styryl-L-β-homoalanine |
| (S)-Fmoc-3,4-difluoro-β-Homophe-OH | (S)-3-(Fmoc-amino)-4-(3,4-difluorophenyl)butyric acid, Fmoc-3,4-difluoro-L-β-Homophe-OH |
| (S)-Fmoc-4-chloro-β-Homophe-OH | (S)-3-(Fmoc-amino)-4-(4-chlorophenyl)butyric acidFmoc-4-chloro-L-β-Homophe-OH |
| Fmoc-4-Abz-OH | 4-(Fmoc-amino)benzoic acid |
| (R)-Fmoc-4-(3-pyridyl)-β-Homoala-OH | (R)-3-(Fmoc-amino)-4-(3-pyridyl)butyric acid, Fmoc-4-(3-pyridyl)-D-β-homoalanine |
| 4-(Fmoc-aminomethyl) benzoic acid | 4-(Fmoc-aminomethyl)benzoic acid |
| Fmoc-homocycloleucine | 1-(Fmoc-amino)cyclohexanecarboxylic acid |
| Fmoc-β-(3-benzothienyl)-D-Ala-OH | Fmoc-3-(3-benzothienyl)-D-alanine |

Use of purified fusion proteins as substrates will allow for further characterization of the novel fusion substrates. Mass spectrometry and gel electrophoresis will be used on the purified proteins to measure the efficiency of the cleavage reaction.

Example 10

Identification of Luminogenic Protein Substrates

Genetically engineered variants of recombinant luciferase protein that become activated by specific cleavage reactions are obtained using the following strategies: 1) complementation of inactive luciferase fragments to restore active luciferase molecules; and 2) specific reactions to release the D-luciferin as a substrate for firefly luciferase (FFL from *Photinus pyralis*).

Split FFL constructs are designed and used to detect presence of a specific proteolytic activity. Mutants of FFL can be used to emit light at distinct wavelength varying from greenish-yellow (~560 nm) to orange and red (605 to 613 nm) which allows multiplex detection of several agents on a single device. Also, the color of the light emitted by *Renilla reniformis* (sea pansy) luciferase (RLuc) can be tuned by the chemical environment in which the light-emitting coelenterazine oxidation is performed (Miyaki et al., "Bringing bioluminescence into the picture," *Nature Methods*, 4:616-617 (2007)).

Using this cloning strategy, a set of rSNAP-25/FFL fusion constructs were generated with pETblue-2 and pET28a expression vectors. Because co-expression of overlapping split FFL domains reconstitutes active FFL, an overlapping FFL fusion construct that is interrupted by an integral SNAP-25 sequence containing the BoNT/A cleavage site (within SNAP-25 residues 187 to 206) was cloned and expressed. The resulting fusion protein encompasses FFL[1-475]SNAP-25[187-206]FFL[265-550] (brackets denote the amino acid ranges). In addition an overlapping FFL fusion protein encompassing FFL[1-478]SNAP-25[187-206]FFL[265-550] was constructed (SEQ ID NO: 3) and expressed as product (SEQ ID NO: 4).

A fusion protein containing N-terminal SNAP25[187-206] followed by full length FFL[1]550] was also designed and tested to determine whether N-terminal SNAP-25 can alter FFL activity. Strong signals were obtained from bacterial expressing the fusion protein SNAP-25[187-206]-FFL[1-550], with signal doubling in intensity when in presence of BoNT/A complex. Overlapping split FFL construct FFL[1-475]-SNAP25[187-206]-FFL[265-550] also produced a clear nearly two-fold signal increase in presence of BoNT/A. Overlapping split FFL construct FFL[1-478]-SNAP25[187-206]-FFL[265-550] (SEQ ID NO: 4) also produced a significant increased signal in presence of BoNT/A. The construct FFL[1-475]-SNAP25[187-206] produced an insignificant signal when in presence or absence of BoNT/A treatment.

FIG. 12 provides a synthesis schematic for recombinant overlapping luciferase fragments having an interspaced SNAP25 sequence for BoNT/A detection. For other BoNT serotypes, the corresponding sequences from the appropriate SNARE complex molecule are used.

Example 11

Expandable Bioluminescent Detection System

A dual-strategy approach was employed to create an expandable bioluminescent detection system for the detection of toxin or protease activity. This system was initially developed for detection of BoNT/A as a model, and can readily expandable to detection of all BoNT classes and subtypes as well as other toxins or enzymes having measurable activity. Strategy 1 comprises a dual reaction chamber including 2 vials and two types of beads (FIG. 11A). This strategy uses FFL fusion proteins to recombine and to restore FFL activity similar to previously described methods (Paulmurugan et al., "Combinatorial library screening for developing an improved split-firefly luciferase fragment-assisted complementation system for studying protein-protein interactions," *Anal Chem* 79:2346-2353 (2007); Paulmurugan et al., "Firefly luciferase enzyme fragment complementation for imaging in cells and living animals," *Anal Chem* 77:1295-1302 (2005)). The N-terminal region of FFL that is unable to support bioluminescent reactivity (residues 1 to 475 or shorter) was fused to the binding domain of a known protein having a well characterized binding affinity for another binding partner. The other binding partner was fused to the C-terminal portion of FFL (residues 476 to 550) and to a BoNT/A cleavable SNAP25 sequence (FIG. 11A1). The modified C-terminal FFL fusion was attached to beads via the SNAP25 domain and maintained in a macrofluidic reaction chamber that is capable of interfacing to 1 ml sized sample volumes. Interaction with BoNT/A cleaves the C-terminal FFL fusion, leaving the substrate on the bead surface, to which it has a specific affinity (e.g. by use of a histidine-tag) (FIG. 11A2). Alternatively, the cleaved substrate can be captured on a specific enrichment column. After sufficient exposure to the sample, the accumulated cleaved substrate was eluted and transferred to a microfluidic reaction chamber where it encountered the immobilized N-terminal FFL domain fusion protein. Combination of the FFL fragments occurs through dimerization of the binding protein domains and bioluminescence is detected in the presence of adenosine triphosphate (ATP) and luciferin. The advantage of the dual chamber is that accumulation of cleaved substrate can be obtained over time for samples that do not require further purification, such as, for example, clear serum samples. Turbid samples may require additional purification such as by immuno-capture of the toxin, for which a single chamber (described below) may be more suitable.

In Strategy 2, a single chamber system is employed wherein a luminogenic FFL derivative is directly exposed to affinity-enriched toxin such as BoNT/A (FIG. 11B). The luminogenic FFL derivative can either be constructed directly to the fusion protein or with a fusion of overlapping FFL fragments that are spaced by a cleavable SNAP25 sequence. We have found that the overlapping FFL fragments (1-478) and (265-550) recombine to produce up to 4% of the activity of FFL, possibly by formation of a heterodimer.

Example 12

Detection of Systemic BoNT

Figure 10:
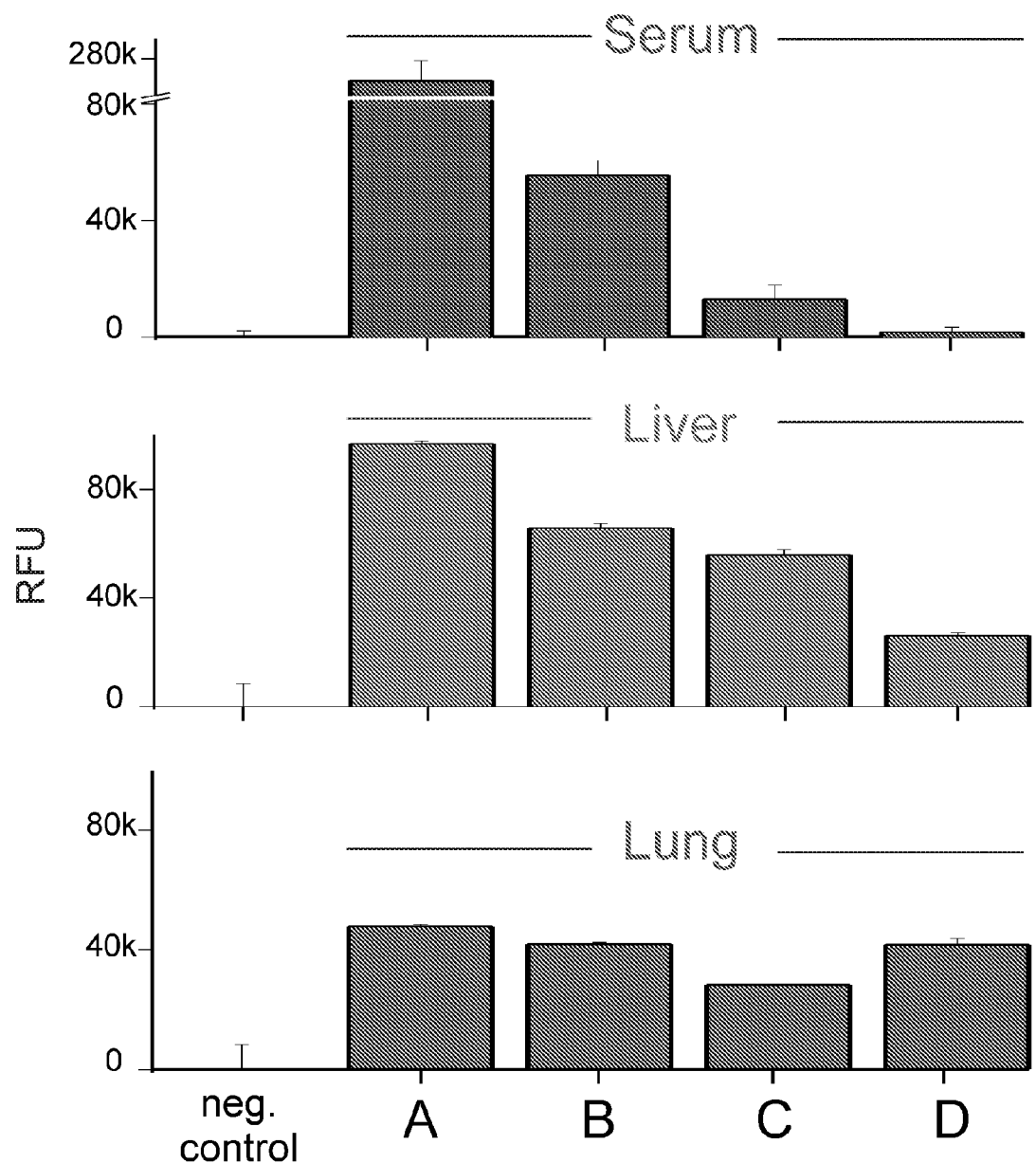
FIG. 10 shows an exemplary BoNT/A ALISSA assay with sera and tissue extracts of intoxicated and non-intoxicated mice. Pairs of mice were i.p. injected with BoNT/A complex in the following amounts: (A) 200 pg; (B) 100 pg; (C) 20 pg; and (D) 0 pg (mock injection). Negative control was reaction buffer only (no serum or organ extracts).

Using the ALISSA method described herein, BoNT/A levels were measured in serum and organs of intoxicated mice. The ALISSA was performed on serum, lung and liver of mice that had been intraperitoneally injected with different doses of BoNT/A complex or with a mock injection of buffer only (control mice). (FIG. 10). Organs were homogenized using the Whirl bag method (Walsh et al., "Tissue homogenization with sterile reinforced polyethylene bags for quantitative culture of *Candida albicans*," *J. Clin Microbiol*. 25:931-932 (1987). BoNT/A was detected systemically as shown in FIG.

10. BoNT/A was detected in blood and liver harvested two hours after injection with toxin. BoNT/A levels in the lung remained low.

Example 13

ALISSA Technology on Additional Targets

Figure 16:
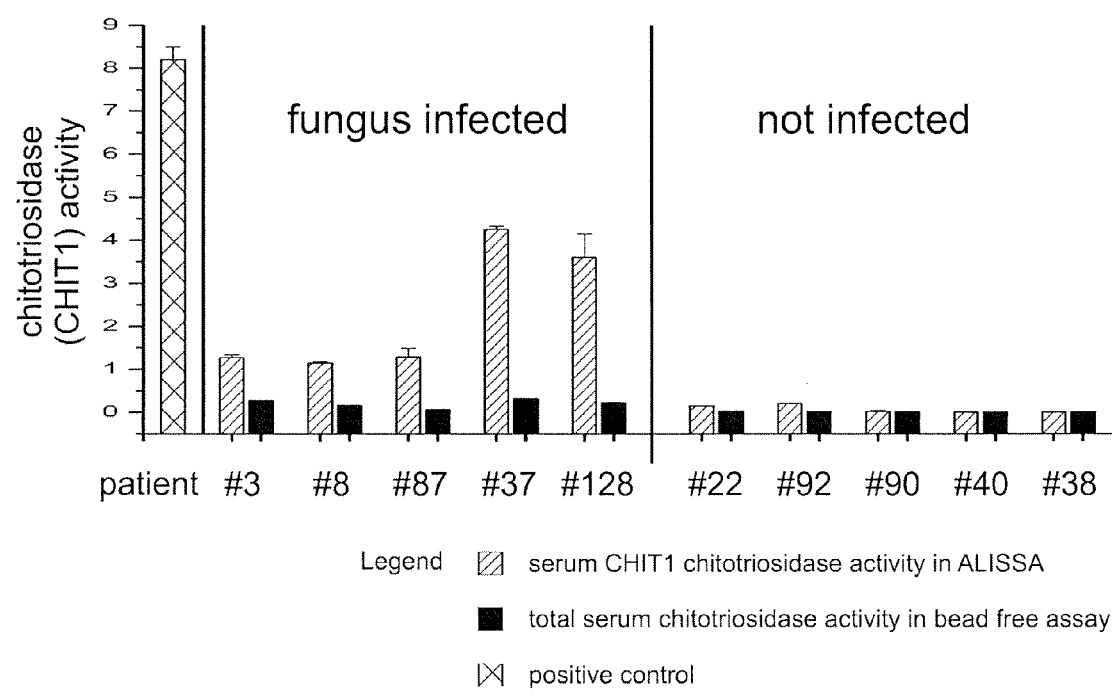
FIG. 16 shows an exemplary ALISSA assay as performed to detect target enzyme chintase. Serum from 10 patients were tested. The patients are identified as "#3", "#8", "#87", "#37", "#128", "#22", "#92", "#90", "#40", and "#38". Hatched bars correspond to CHIT1 serum ALISSA. Solid bars corresponds to serum chitotriosidase activity. Positive control sera is indicated to the far left.
Figure 17:
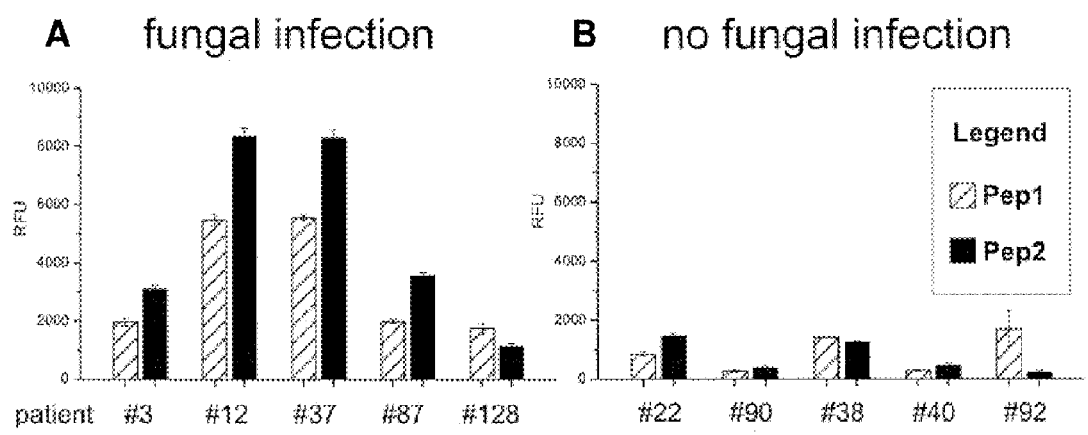
FIG. 17 shows an exemplary ALISSA assay as performed to detect target enzyme Pep1 and Pep2 in patients with fungal infection (A) and no fungal infection (B). Patient sera are identified as "#3", "#12", "#37", "#87", "#128", "#22", "#90", "#38", "#40" and "#92". Hatched bars correspond to Pep1 results. Solid bars correspond to Pep2.

The ALISSA technology is also applicable for use with targets such as enzymes or toxins other than BoNT. Using commercial fluorogenic MAPKKide (List Biological Laboratories) and anthrax lethal factor (LF) as toxin, nanomolar detection limits were achieved. When LF was immobilized on anti-LF-agarose beads, the enzymatic activity of LF was accelerated and detection of femtomolar and lower concentrations was achieved. The ALISSA technology was also extended to detection of human chitinases (e.g. CHIT1 and AMCase) (FIG. 16) and non-metalloproteases (Pep1 and Pep2 of *Aspergillus fumigatus*) (FIG. 17). As shown in FIGS. 16 and 17, the ALISSA technology is applicable for use with a wide variety of targets including non-toxin targets and enzymes.

The examples disclosed herein are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention. All references cited herein are incorporated by reference as if fully set forth herein.

REFERENCES

1. Arnon, S. S. et al. Botulinum toxin as a biological weapon: medical and public health management. *Jama* 285, 1059-1070 (2001).
2. Wein, L. M. & Liu, Y. Analyzing a bioterror attack on the food supply: the case of botulinum toxin in milk. *Proc Natl Acad Sci USA* 102, 9984-9989 (2005).
3. Arnon, S. S., Schechter, R., Maslanka, S. E., Jewell, N. P. & Hatheway, C. L. Human botulism immune globulin for the treatment of infant botulism. *N Engl J Med* 354, 462-471 (2006).
4. Schantz, E. J. & Johnson, E. A. Properties and use of botulinum toxin and other microbial neurotoxins in medicine. *Microbiol. Rev* 56, 80-99 (1992).
5. Sakaguchi, G. *Clostridium botulinum* toxins. *Pharmacol Ther* 19, 165-194 (1982).
6. Chen, F., Kuziemko, G. M. & Stevens, R. C. Biophysical characterization of the stability of the 150-kilodalton botulinum toxin, the nontoxic component, and the 900-kilodalton botulinum toxin complex species. *Infect Immun* 66, 2420-2425 (1998).
7. Sharma, S. K., Ramzan, M. A. & Singh, B. R. Separation of the components of type A botulinum neurotoxin complex by electrophoresis. *Toxicon* 41, 321-331 (2003).
8. Melling, J., Hambleton, P. & Shone, C. C. *Clostridium botulinum* toxins: nature and preparation for clinical use. *Eye* 2 (Pt 1), 16-23 (1988).
9. Zhang, L., Lin, W. J., Li, S. & Aoki, K. R. Complete DNA sequences of the botulinum neurotoxin complex of *Clostridium botulinum* type A-Hall (Allergan) strain. *Gene* 315, 21-32 (2003).
10. Aoki, K. R. & Guyer, B. Botulinum toxin type A and other botulinum toxin serotypes: a comparative review of biochemical and pharmacological actions. *Eur J Neurol* 8 Suppl 5, 21-29 (2001).
11. Smith, L. D. The occurrence of *Clostridium botulinum* and *Clostridium tetani* in the soil of the United States. *Health Lab Sci* 15, 74-80 (1978).
12. Schiavo, G., Matteoli, M. & Montecucco, C. Neurotoxins affecting neuroexocytosis. *Physiol Rev* 80, 717-766 (2000).
13. Kurazono, H. et al. Minimal essential domains specifying toxicity of the light chains of tetanus toxin and botulinum neurotoxin type A. *J Biol Chem* 267, 14721-14729 (1992).
14. Lacy, D. B., Tepp, W., Cohen, A. C., DasGupta, B. R. & Stevens, R. C. Crystal structure of botulinum neurotoxin type A and implications for toxicity. *Nat Struct Biol* 5, 898-902 (1998).
15. Cai, S., Sarkar, H. K. & Singh, B. R. Enhancement of the endopeptidase activity of botulinum neurotoxin by its associated proteins and dithiothreitol. *Biochemistry* 38, 6903-6910 (1999).
16. Cai, S. & Singh, B. R. Role of the disulfide cleavage induced molten globule state of type a botulinum neurotoxin in its endopeptidase activity. *Biochemistry* 40, 15327-15333 (2001).
17. Ferreira, J. L., Maslanka, S., Johnson, E. & Goodnough, M. Detection of botulinal neurotoxins A, B, E, and F by amplified enzyme-linked immunosorbent assay: collaborative study. *J AOAC Int* 86, 314-331 (2003).
18. Kautter, D. A. & Solomon, H. M. Collaborative study of a method for the detection of *Clostridium botulinum* and its toxins in foods. *J Assoc Off Anal Chem* 60, 541-545 (1977).
19. Sharma, S. K., Ferreira, J. L., Eblen, B. S. & Whiting, R. C. Detection of type A, B, E, and F *Clostridium botulinum* neurotoxins in foods by using an amplified enzyme-linked immunosorbent assay with digoxigenin-labeled antibodies. *Appl Environ Microbiol* 72, 1231-1238 (2006).
20. Sugiyama, H. *Clostridium botulinum* neurotoxin. *Microbiol. Rev* 44, 419-448 (1980).
21. Varnum, S. M. et al. Enzyme-amplified protein microarray and a fluidic renewable surface fluorescence immunoassay for botulinum neurotoxin detection using high-affinity recombinant antibodies. *Analytica Chimica Acta* 570, 137-143 (2006).
22. Kalb, S. R. et al. The use of Endopep-MS for the detection of botulinum toxins A, B, E, and F in serum and stool samples. *Anal Biochem* 351, 84-92 (2006).
23. Barr, J. R. et al. Botulinum neurotoxin detection and differentiation by mass spectrometry. *Emerg Infect Dis* 11, 1578-1583 (2005).
24. Kalb, S. R., Goodnough, M. C., Malizio, C. J., Pirkle, J. L. & Barr, J. R. Detection of botulinum neurotoxin A in a spiked milk sample with subtype identification through toxin proteomics. *Anal Chem* 77, 6140-6146 (2005).
25. Boyer, A. E. et al. From the mouse to the mass spectrometer: detection and differentiation of the endoproteinase activities of botulinum neurotoxins A-G by mass spectrometry. *Anal Chem* 77, 3916-3924 (2005).
26. Chao, H. Y., Wang, Y. C., Tang, S. S. & Liu, H. W. A highly sensitive immuno-polymerase chain reaction assay for *Clostridium botulinum* neurotoxin type A. *Toxicon* 43, 27-34 (2004).
27. Mason, J. T., Xu, L., Sheng, Z. M. & O'Leary, T. J. A liposome-PCR assay for the ultrasensitive detection of biological toxins. *Nat Biotechnol* 24, 555-557 (2006).
28. Mason, J. T., Xu, L., Sheng, Z. M., He, J. & O'Leary, T. J. Liposome polymerase chain reaction assay for the sub-attomolar detection of cholera toxin and botulinum neurotoxin type A. *Nature Protocols* 1, 2003-2011 (2006).

29. Ekong, T. A., McLellan, K. & Sesardic, D. Immunological detection of *Clostridium botulinum* toxin type A in therapeutic preparations. *J Immunol Methods* 180, 181-191 (1995).
30. Schmidt, J. J. & Stafford, R. G. Fluorigenic substrates for the protease activities of botulinum neurotoxins, serotypes A, B, and F. *Appl Environ Microbiol* 69, 297-303 (2003).
31. Schiavo, G. et al. Identification of the nerve terminal targets of botulinum neurotoxin serotypes A, D, and E. *J Biol Chem* 268, 23784-23787 (1993).
32. Schiavo, G. et al. Botulinum neurotoxins serotypes A and E cleave SNAP-25 at distinct COOH-terminal peptide bonds. *FEBS Lett* 335, 99-103 (1993).

We claim:

1. A method for detecting the presence of a botulinum toxin in a sample comprising:

a) exposing the sample putatively containing a botulinum toxin to (i) an enrichment matrix comprising a botulinum-specific antibody that captures botulinum toxin in the sample and (ii) a substrate composition comprising a toxin substrate that is capable of eliciting a detectable fluorogenic signal when modified by the botulinum toxin, the substrate selected from (SEQ ID NO: 12)
Lys[5-Fam]IleAspGluAlaAsnGlnArgAlaThrLys[DABCYL]X,
wherein X is norleucine;

(SEQ ID NO: 13)
5-Fam-
Lys[5-Fam]IleAspGluAlaAsnGlnArgAlaThrLys[DABCYL]X,
wherein X is norleucine; or (SEQ ID NO: 14)
5-Fam-LysIleAspGluAlaAsnGlnArgAlaThrLys[DABCYL]Nle, wherein the exposure occurs under conditions permitting binding of the botulinum toxin to the antibody and modification of the substrate by the botulinum toxin; and b) detecting the presence of the botulinum toxin by measuring a change in fluorescence in the sample.

2. The method of claim 1 wherein the sample is exposed to the enrichment matrix prior to being exposed to the substrate.

3. The method of claim 1 wherein the toxin retains measurable enzymatic activity subsequent to its binding by the antibody.

4. The method of claim 1 wherein said toxin is botulinum neurotoxin serotype A (BoNT/A).

5. The method of claim 1 wherein the enrichment matrix comprises anti-BoNT/A antibodies bound to bead-immobilized protein A molecules.

6. The method of claim 1 wherein the matrix is an immunosorbent support comprised of loose beads or a fixed column.

7. The method of claim 1 wherein the substrate composition further comprises a control substrate having the sequence:

```
                                            (SEQ ID NO: 15)
5-Fam-
Lys[5-Fam]IleAspGluAlaAsnGlnGluLeuThrLys[DABCYL]Nle.
```

8. The method of claim 1 wherein the substrate composition further comprises a substrate that is capable of eliciting a detectable luminogenic signal when modified by the botulinum toxin, the substrate selected from SEQ ID NO:3 or SEQ ID NO:4; and wherein detection of the presence of botulinum toxin is accomplished by measuring a change in light emission in the sample.

9. A method for detecting the presence of a botulinum toxin in a sample comprising:

a) exposing the sample putatively containing a botulinum toxin to (i) an enrichment matrix comprising a botulinum-specific antibody that captures botulinum toxin in the sample and (ii) a substrate composition comprising substrate that is capable of eliciting a detectable fluorogenic signal when modified by the botulinum toxin, the substrate comprising a control substrate having the sequence 5-Fam-Lys[5-Fam]IleAspGluAlaAsnGlnGluLeuThrLys[DABCYL]Nle (SEQ ID NO:15), wherein the exposure occurs under conditions permitting binding of the botulinum toxin to the antibody and modification of the substrate by the botulinum toxin; and b) detecting the presence of the botulinum toxin by measuring a change in fluorescence or light emission in the sample.

10. The method of claim 9 wherein the substrate composition further comprises a substrate that is capable of eliciting a detectable fluorogenic signal when modified by the botulinum toxin, the substrate selected from

```
                                            (SEQ ID NO: 12)
Lys[5-Fam]IleAspGluAlaAsnGlnArgAlaThrLys[DABCYL]X,
wherein X is norleucine;

(SEQ ID NO: 13)
5-Fam-
Lys[5-Fam]IleAspGluAlaAsnGlnArgAlaThrLys[DABCYL]X,
wherein X is norleucine; or (SEQ ID NO: 14)
5-Fam-LysIleAspGluAlaAsnGlnArgAlaThrLys[DABCYL]Nle.
```

11. The method of claim 9 wherein the substrate composition further comprises a toxin substrate that is capable of eliciting a detectable luminogenic signal when modified by the botulinum toxin, the substrate selected from SEQ ID NO:3 or SEQ ID NO:4, and wherein detection of the presence of botulinum toxin is accomplished by measuring a change in light emission in the sample.

12. The method of claim 9 wherein the sample is exposed to the enrichment matrix prior to being exposed to the substrate.

13. The method of claim 9 wherein the toxin retains measurable enzymatic activity subsequent to its binding by the antibody.

14. The method of claim 9 wherein said toxin is botulinum neurotoxin serotype A (BoNT/A).

15. The method of claim 9 wherein the enrichment matrix comprises anti-BoNT/A antibodies bound to bead-immobilized protein A molecules.

16. The method of claim 9 wherein the matrix is an immunosorbent support comprised of loose beads or a fixed column.

* * * * *

UNITED STATES PATENT AND TRADEMARK OFFICE
CERTIFICATE OF CORRECTION

PATENT NO. : 8,067,192 B2
APPLICATION NO. : 12/134092
DATED : November 29, 2011
INVENTOR(S) : Kalkum et al.

It is certified that error appears in the above-identified patent and that said Letters Patent is hereby corrected as shown below:

In the Specification

In the Government Interest section, Column 1, Lines 12-14, please delete:
"The present invention was supported by National Institutes of Health grant AI-65359. The government may have certain rights in the present invention."
And replace with:
--This invention was made with government support under AI065359 awarded by the National Institutes of Health. The government has certain rights in the invention.--

Signed and Sealed this
Twenty-second Day of November, 2022

Katherine Kelly Vidal
*Director of the United States Patent and Trademark Office*